(12) United States Patent
Goldstein et al.

(10) Patent No.: US 6,796,168 B1
(45) Date of Patent: Sep. 28, 2004

(54) METHOD FOR DETERMINING A CHARACTERISTIC VISCOSITY-SHEAR RATE RELATIONSHIP FOR A FLUID

(75) Inventors: Larry J. Goldstein, Doylestown, PA (US); William N. Hogenauer, Gilbertsville, PA (US)

(73) Assignee: Rheologics, Inc., Exton, PA (US)

( * ) Notice: Subject to any disclaimer, the term of this patent is extended or adjusted under 35 U.S.C. 154(b) by 73 days.

(21) Appl. No.: 10/245,237

(22) Filed: Sep. 17, 2002

Related U.S. Application Data

(63) Continuation-in-part of application No. 09/897,164, filed on Jul. 2, 2001, now Pat. No. 6,484,565, which is a continuation-in-part of application No. 09/789,350, filed on Feb. 21, 2001, now abandoned.
(60) Provisional application No. 60/228,612, filed on Aug. 29, 2000.

(51) Int. Cl.[7] .............................................. G01N 11/00
(52) U.S. Cl. .................... 73/54.01; 73/54.01; 73/54.02; 73/54.07; 73/54.14; 73/54.04; 324/71.1
(58) Field of Search ........................... 73/54.01, 54.02, 73/54.07, 54.14, 71.1, 54.04

(56) References Cited

U.S. PATENT DOCUMENTS

| | | |
|---|---|---|
| 1,810,992 A | 6/1931 | Dallwitz-Wegner |
| 2,343,061 A | 2/1944 | Irany |
| 2,696,734 A | 12/1954 | Brunstrum et al. |
| 2,700,891 A | 2/1955 | Shafer |
| 2,934,944 A | 5/1960 | Eolkin |
| 3,071,961 A | 1/1963 | Heigl et al. |
| 3,116,630 A | 1/1964 | Piros |
| 3,137,161 A | 6/1964 | Lewis et al. |
| 3,138,950 A | 6/1964 | Welty et al. |
| 3,277,694 A | 10/1966 | Cannon et al. |
| 3,286,511 A | 11/1966 | Harkness |
| 3,342,063 A | 9/1967 | Smythe et al. |
| 3,435,665 A | 4/1969 | Tzentis |
| 3,520,179 A | 7/1970 | Reed |
| 3,604,247 A | 9/1971 | Gramain et al. |
| 3,666,999 A | 5/1972 | Moreland, Jr. et al. |

(List continued on next page.)

FOREIGN PATENT DOCUMENTS

| | | |
|---|---|---|
| DE | 31 38514 A1 | 4/1983 |
| EP | 0 654 286 A1 | 12/1994 |
| FR | 2 510 257 | 1/1983 |
| WO | WO 92/15878 | 9/1992 |
| WO | WO 94/20832 | 9/1994 |
| WO | WO 99/10724 | 3/1999 |

OTHER PUBLICATIONS

A Capillary Viscometer with Continuously Varying Pressure Head, Maron, et al., vol. 25, No. 8, Aug., 1954.

(List continued on next page.)

*Primary Examiner*—Hezron Williams
*Assistant Examiner*—André K. Jackson
(74) *Attorney, Agent, or Firm*—Caesar, Rivise, Bernstein, Cohen & Pokotilow, Ltd.

(57) ABSTRACT

A method for determining the viscosity of a fluid flowing through a system at any point in the system whereby the method involves determining a characteristic relationship for the fluid between viscosity and shear rate; obtaining a shear rate of the fluid as it moves through at least one position in the system; and determining the viscosity of fluid at the at least one position by applying the shear rate to the characteristic relationship. Where the system is the circulatory system of a living being, the method includes determining a viscosity-shear rate relationship unique to that individual. Furthermore, the method further entails determining the actual viscosities and shear rates being experienced in selected blood vessels of the living being.

7 Claims, 9 Drawing Sheets

U.S. PATENT DOCUMENTS

| | | |
|---|---|---|
| 3,680,362 A | 8/1972 | Geerdes et al. |
| 3,699,804 A | 10/1972 | Gassmann et al. |
| 3,713,328 A | 1/1973 | Aritomi |
| 3,720,097 A | 3/1973 | Kron |
| 3,782,173 A | 1/1974 | Van Vessem et al. |
| 3,839,901 A | 10/1974 | Finkle et al. |
| 3,908,411 A | 9/1975 | Virloget |
| 3,911,728 A | 10/1975 | Fixot |
| 3,952,577 A | 4/1976 | Hayes et al. |
| 3,967,934 A | 7/1976 | Seitz et al. |
| 3,990,295 A | 11/1976 | Renovanz et al. |
| 3,999,538 A | 12/1976 | Philpot, Jr. |
| 4,083,363 A | 4/1978 | Philpot, Jr. |
| 4,149,405 A | 4/1979 | Ringrose |
| 4,165,632 A | 8/1979 | Weber et al. |
| 4,193,293 A | 3/1980 | Cavallari |
| 4,207,870 A | 6/1980 | Eldridge |
| 4,302,965 A | 12/1981 | Johnson et al. |
| 4,341,111 A | 7/1982 | Husar |
| 4,417,584 A | 11/1983 | Cathignol et al. |
| 4,426,878 A | 1/1984 | Price et al. |
| 4,432,761 A | 2/1984 | Dawe |
| 4,461,830 A | 7/1984 | Philpot, Jr. |
| 4,517,830 A | 5/1985 | Gunn, deceased et al. |
| 4,519,239 A | 5/1985 | Kiesewetter et al. |
| 4,554,821 A | 11/1985 | Kiesewetter et al. |
| H93 H | 7/1986 | Matta et al. |
| 4,616,503 A | 10/1986 | Plungis et al. |
| 4,637,250 A | 1/1987 | Irvine, Jr. et al. |
| 4,680,957 A | 7/1987 | Dodd |
| 4,680,958 A | 7/1987 | Ruelle et al. |
| 4,750,351 A | 6/1988 | Ball |
| 4,856,322 A | 8/1989 | Langrick et al. |
| 4,858,127 A | 8/1989 | Kron et al. |
| 4,884,577 A | 12/1989 | Merrill |
| 4,899,575 A | 2/1990 | Chu et al. |
| 4,947,678 A | 8/1990 | Hori et al. |
| 5,099,698 A | 3/1992 | Kath et al. |
| 5,222,497 A | 6/1993 | Ono |
| 5,224,375 A | 7/1993 | You et al. |
| 5,257,529 A | 11/1993 | Taniguchi et al. |
| 5,271,398 A | 12/1993 | Schlain et al. |
| 5,272,912 A | 12/1993 | Katsuzaki |
| 5,327,778 A | 7/1994 | Park |
| 5,333,497 A | 8/1994 | Br nd Dag A. et al. |
| 5,365,776 A | 11/1994 | Lehmann et al. |
| 5,421,328 A | 6/1995 | Bedingham |
| 5,447,440 A | 9/1995 | Davis et al. |
| 5,491,408 A | 2/1996 | Rousseau |
| 5,494,639 A | 2/1996 | Grzegorzewski |
| 5,629,209 A | 5/1997 | Braun, Sr. et al. |
| 5,686,659 A | 11/1997 | Neel et al. |
| 5,725,563 A | 3/1998 | Klotz |
| 5,792,660 A | 8/1998 | Spillert et al. |
| 6,019,735 A | 2/2000 | Kensey et al. |
| 6,077,234 A | 6/2000 | Kensey |
| 6,152,888 A | 11/2000 | Kensey et al. |
| 6,193,667 B1 | 2/2001 | Kensey |
| 6,200,277 B1 | 3/2001 | Kensey |
| 6,261,244 B1 | 7/2001 | Kensey et al. |
| 6,322,524 B1 | 11/2001 | Kensey et al. |
| 6,322,525 B1 | 11/2001 | Kensey et al. |
| 6,402,703 B1 | 6/2002 | Kensey et al. |
| 6,412,336 B2 | 7/2002 | Shin et al. |
| 6,428,488 B1 | 8/2002 | Kensey et al. |
| 6,443,911 B1 | 9/2002 | Kensey et al. |
| 6,450,974 B1 | 9/2002 | Kim et al. |
| 6,484,565 B2 | 11/2002 | Shin et al. |
| 6,484,566 B1 | 11/2002 | Shin et al. |

OTHER PUBLICATIONS

Colloid Symposium Monograph, P. Glesy, et al., vol. V, p. 253, 1928.

Kolloid–Zeitschrift, Prof. Dr. Wolfgang Ostwald, Band XLI, Leipzig University, 1927.

Kensey, et al., Effects of whole blood viscosity on atherogenesis, Jnl. Of Invasive Cardiol. V. 9,17, 1997.

Ernst. et al., Cardiovascular Risk Factors & Hemorrheology: Physical Fitness, Stress & Obesity, Atheros. V. 59, 263–269, 1986.

Levenson, et al., Cigarette Smoking & Hypertension, Atherosclerosis V. 7, 572–577, 1987.

Rillaerts, et al., Blood viscosity in Human Obesity; relation to glucose Tolerance and Insulin Status, Internl Jnl. Of Obesity, V. 13, 739–741, 1989.

Rosenson. R., Viscosity & Ischemic Heart Disease, Jnl. Of Vascular Medicine & Biol., V. 4, 206–212, 1993.

Letcher, et al., Direct Relationship Between Blood Pressure & Blood Viscosity in Normal & Hypertensive Subjects, Am. Jnl of Med. V. 70, 1195–1203, Jun. 1981.

Zwick, K.J., The Fluid Mechanics of Bonding with Yield Stress Exposies, Dissortation, Un. Of Penn., PA, USA, 1–142, 1996.

Yarnell, et al., Fibrinogen, viscosity & White Blood Cell Count are Major Risk Factors for Ischemic Heart Disease, Circulation, V. 83, No. 3, Mar. 1991.

Tangney, et al., Postprandial changes in Plasma & Serum Viscosity & Plasma Lipids & Lipoproteins after an acute test meal, Am. Jnl. Of Clin. Nutrition V. 65, 36–40, 1997.

Seplowitz, et al., Effects of Lipoproteins on Plasma Viscosity, Atherosclerosis, V. 38, 89–95, 1981.

Rosenson, et al., Hyperviscosity Syndrome in Hypercholesterolemic Patient with Primary Biliary Cirrhosis, Gastroenterology, V. 98, No. 5, 1990.

Lowe, et al., Blood Viscosity & Risk of Cardiovascular Events: the Edinburgh Artery Study, British Jnl. Of Haematology, V. 96, 168–173, 1997.

Koenig, W., Blood Rheology Assoc. with Cardiovascular Risk Factors & Chronic Cardiovascular Diseases: Results of an Epidemiologic Cross Sectional Study, Am. Coll. Of Angiology, Paradise Is., Bahamas, Oct. 1997.

Hell, K., Importance of Blood Viscoelasticity in Arteriosclerosis, Internl Coll. Of Angiology , Montreux, Switzerland, Jul. 1987.

Delaunois, A., Thermal method for Continuous Blood velocity Measurements in Large Blood Vessels & Cardiac Output Determination, Medical & Biological Engineering, Mar. 1973, V. 11, 201–205.

Nerem, et al., Fluid Mechanics in Atherosclerosis, Handbook of Bioengineering, Chp. 21, 20.24 to 21.22.

Litt, et al., Theory & Design of Disposable Clinical Blood Viscometer, Biorheology, V. 25, 697–712, 1988.

Cooke, et al., Automated Measurement of Plasma Viscosity by Capillary Viscometer, J. Clin. Path., vol. 341, 1213–1216, 1988.

Jiminez, et al., A novel computerized Viscometer/rheometer, Rev. sci. Instrum. V. 65, (1), 229–241, Jan. 1994.

Harkness, A New Instrument for Measurement of Plasma–Viscosity, Med. & Biol. Engineering, Sep. 1976.

Pringle, et al., Blood Viscosity & Raynaud's Disease, The Lancet, May 1965.

Walker, et al., Measurement of Blood Viscosity using a conicylindrical viscometer, Med & Biol: Engineering, Sep. 1976.

Oguraa, et al., Measurement of Human Red Blood Cell Deformability using a Single Micropore on a Thin Si3N4 Film, IEEE Transactions on Biomedical Engineering, V. 38, No. 9, Aug. 1991.

Hausler, et al., A Newly Designed Oscillating Viscometer for Blood Viscosity Measurements, 1999 V. 33, No. 4, Biorheology, p. 397–404.

Martin, et al., Apparent Viscosity of Whole Human Blood at Various Hydrostatic Pressures I. Studies on Anticoagulated Blood Employing new Capillary Viscometer, Biorheology 3–12, V. 11, 1978.

Rheinhardt, et al., Rheologic Measurements on Small Samples with a New Capillary Viscometer, J.Lab. And Clin. Med., 921–931, Dec. 1984.

Pall Corporation, Pall BPF4 High Efficiency Leukocyte Removal Blood Processing Filter System, Pall Biomedical Products Corporation 1993.

Qamar, et al., The Goldman Algorithm Revisited: Prospective E#valuation of Computer Derived Algorithm Vs. Unaided Physician Judgement in Suspected Acute Myocardial Inf., AM. Hrt J. 138, V. 4, 705–709.

Leonhardt, et al., Studies on Plasma Viscosity in Primary Hyperlipoproteinaemia, Atherosclerosis, V.28, 29–40, 1977.

Fung, Y.C., Biomechanics, Mechanical Properties of Living Tissues, Second Edition.-

METHOD FOR DETERMINING A CHARACTERISTIC VISCOSITY-SHEAR RATE RELATIONSHIP FOR A FLUID

RELATED APPLICATIONS

This application is a Continuation-in-Part of application Ser. No. 09/897,164, filed Jul. 2, 2001, now U.S. Pat. No. 6,484,565, entitled SINGLE RISER/SINGLE CAPILLARY VISCOMETER USING MASS DETECTION OR COLUMN HEIGHT DETECTION, which in turn is a Continuation-In-Part of application Ser. No. 09/789,350, filed Feb. 21, 2001, entitled Mass Detection Capillary Viscometer, now abandoned, which in turn is based on Provisional Application Serial No. 60/228,612 filed Aug. 29, 2000 entitled MASS DETECTION CAPILLARY VISCOMETER. The entire disclosures of all the above applications are incorporated by reference herein and are assigned to the same Assignee as the present application, namely, Rheologics, Inc.

BACKGROUND OF THE INVENTION

1. Field of Invention

This invention relates generally to methods for measuring the viscosity of fluids, and more specifically, to a method for determining the viscosity of a fluid flowing through a system at any point in the system.

2. Description of Related Art

A capillary viscometer is commonly used because of its inherent features such as simplicity, accuracy, similarity to process flows like extrusion dies, no free surface, etc. Viscous flow in capillary viscometry is firmly established both theoretically and experimentally. C. W. Macosko, *Rheology: Principles, Measurements, and Applications* (VCH, 1993). In fact, the capillary viscometer was the first viscometer and this device remains the most common for measuring viscosity for polymer solutions and other non-Newtonian fluids. However, most existing capillary viscometers produce viscosity measurement a shear rate at a time. In the case of Newtonian fluids the observation of the rate of flow at a single pressure drop is sufficient to define the flow behavior. However, in the case of non-Newtonian fluids, viscosity measurements need to be performed over a range of shear rates. In order to measure viscosity over a range of shear rates, it is necessary to repeat the measurement by varying either the driving pressure head or the capillary tube diameter, which leads to a time-consuming measurement requiring intensive labor. Hence, these methods are not suited for measuring the rheology of polymer fluids that may exhibit shear-dependent viscosities. Furthermore, application of such techniques often requires relatively large volumes of the test fluids. Therefore, there has been a need to develop a simple and labor-free viscometer which can measure the viscosity of fluids over shear rates at a time.

In U.S. Pat. No. 6,019,735 (Kensey et al.) and U.S. Pat. No. 6,077,234 (Kensey et al.), which are assigned to the same Assignee, namely Rheologics, Inc., of the present invention, there is disclosed a scanning-capillary-tube viscometer for measuring the viscosity of a fluid, e.g., circulating blood of a living being. Among other things, this scanning capillary tube viscometer discloses an apparatus that monitors the changing height of a column of fluid versus time in a riser that is in fluid communication with a living being's circulating blood. A further improvement of this type of scanning capillary tube viscometer is disclosed in U.S. Pat. No. 6,322,524 (Kensey et al.) and U.S. Pat. No. 6,402,703 (Kensey et al.), both entitled DUAL RISER/SINGLE CAPILLARY VISCOMETER, which are assigned to the same Assignee as the present invention, namely, Rheologics, Inc. and whose entire disclosures are incorporated by reference herein. In those patents, a U-shaped tube structure is utilized that generates a falling and rising column of test fluid that is driven by a decreasing pressure differential for moving these columns of fluid through a plurality of shear rates, which is necessary for non-Newtonian fluid (e.g., blood) viscosity determinations. Such an apparatus can produce viscosity data in a low shear range (e.g., approximately 0.2 $s^{-1}$).

However, there remains a need, especially in the field of blood rheology, for determining a unique viscosity-shear rate relationship for a particular fluid in a system that describes the fluid viscosity over a wide range of shear rates. For example, it would be extremely desirable to have a unique viscosity-shear rate relationship for the circulating blood of an individual. By determining such a unique relationship, a physician could accurately determine the viscosity at any particular location in the individual's circulatory system by simply measuring the shear rate of the circulating blood at that location and then plugging that shear rate into that individual's unique viscosity-shear rate relationship. Moreover, by taking a plurality of shear rate measurements throughout the individual's circulatory system, determining the respective viscosities and then multiplying these viscosities by the respective shear rates, a physician can also develop a shear stress profile for that individual's circulatory system.

BRIEF SUMMARY OF THE INVENTION

A method for determining the viscosity of a fluid flowing through a system at any point in the system. The method comprises the steps of: (a) determining a characteristic relationship for the fluid between viscosity and shear rate; (b) obtaining a shear rate of the fluid as it moves through at least one position in the system; and (c) determining the viscosity of the fluid at the at least one position by applying the shear rate to the characteristic relationship.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

The method 120 (FIG. 3) of the present invention involves utilizing "scanning capillary tube viscometers" which are owned by the same Assignee of the present invention, namely, Rheologics, Inc. of Exton, Pa. Examples of scanning capillary tube viscometers are the subject matter of the following U.S. patents and patent applications:

U.S. Pat. No. 6,322,524 (Kensey et al.): Dual Riser/Single Capillary Viscometer;

U.S. Pat. No. 6,402,703 (Kensey et al.): Dual Riser/Single Capillary Viscometer;

application Ser. No. 09/615,340: Dual Riser/Dual Capillary Viscometer for Newtonian & Non-Newtonian Fluids;

application Ser. No. 09/897,164: Single Riser/Single Capillary Viscometer Using Mass Detection or Column Height Detection;

application Ser. No. 09/897,176: Single Riser/Single Capillary Blood Viscometer Using Mass Detection or Column Height Detection;

application Ser. No. 09/908,374: Single Capillary Tube Viscometer

As referred to throughout this Specification, scanning capillary tube viscometers (hereinafter "SCTVs") operate by subjecting the fluid under test (e.g., circulating blood of a living being) to a plurality of shear rates using a decreasing pressure differential. The device monitors or detects the movement of the fluid under test as it experiences the plurality of shear rates and then from this movement, as well as using known dimensions of the passageways in the device, the viscosity of the fluid under test can be accurately and quickly determined. The diverted fluid remains unadulterated throughout the analysis.

Figure 1:
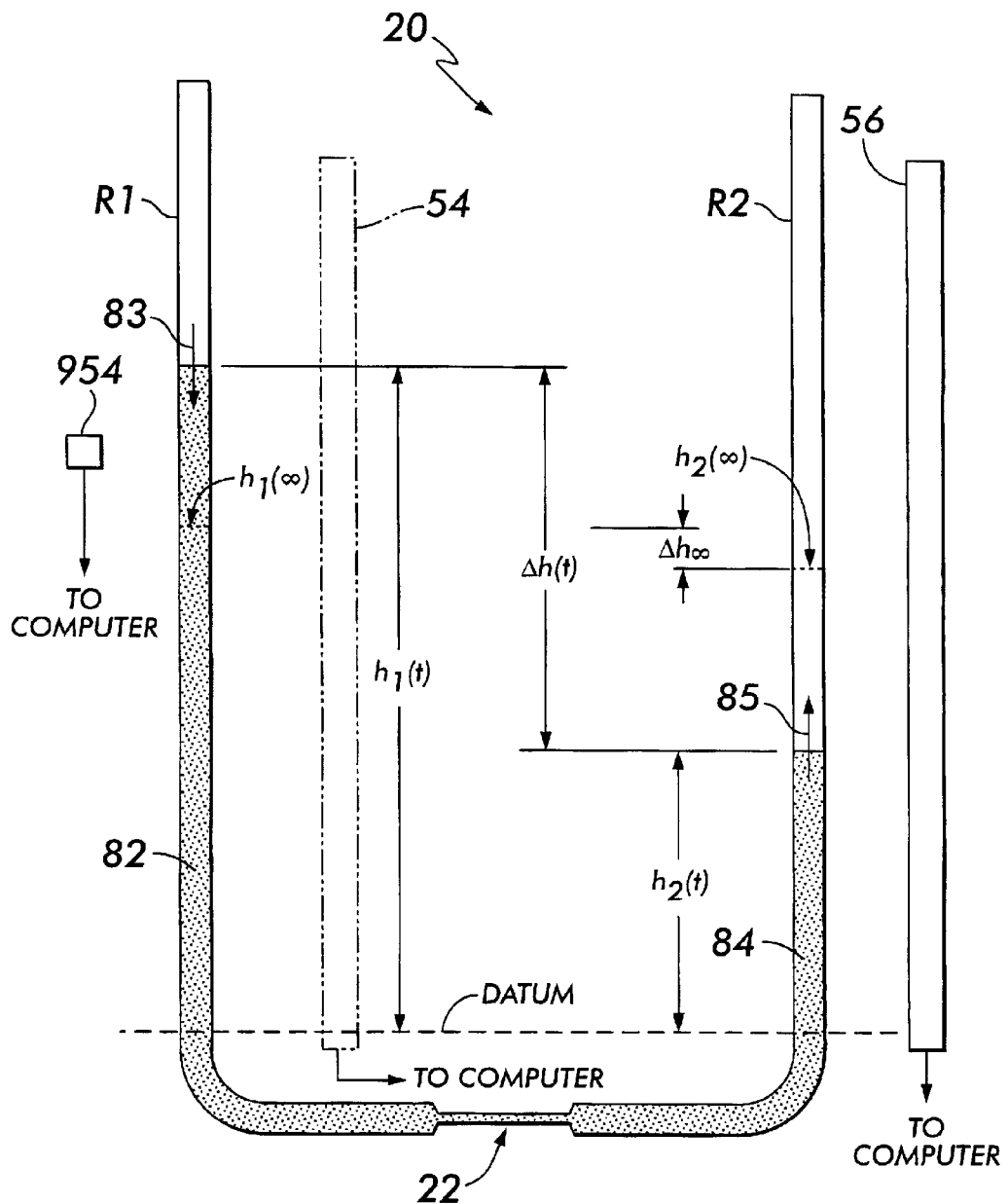
FIG. 1 is a functional diagram of a test fluid flowing in an exemplary scanning tube viscometer (SCTV), e.g., a U-shaped tube having a capillary tube therein and with column level detectors and a single point detector monitoring the movement of the fluid.
Figure 2:
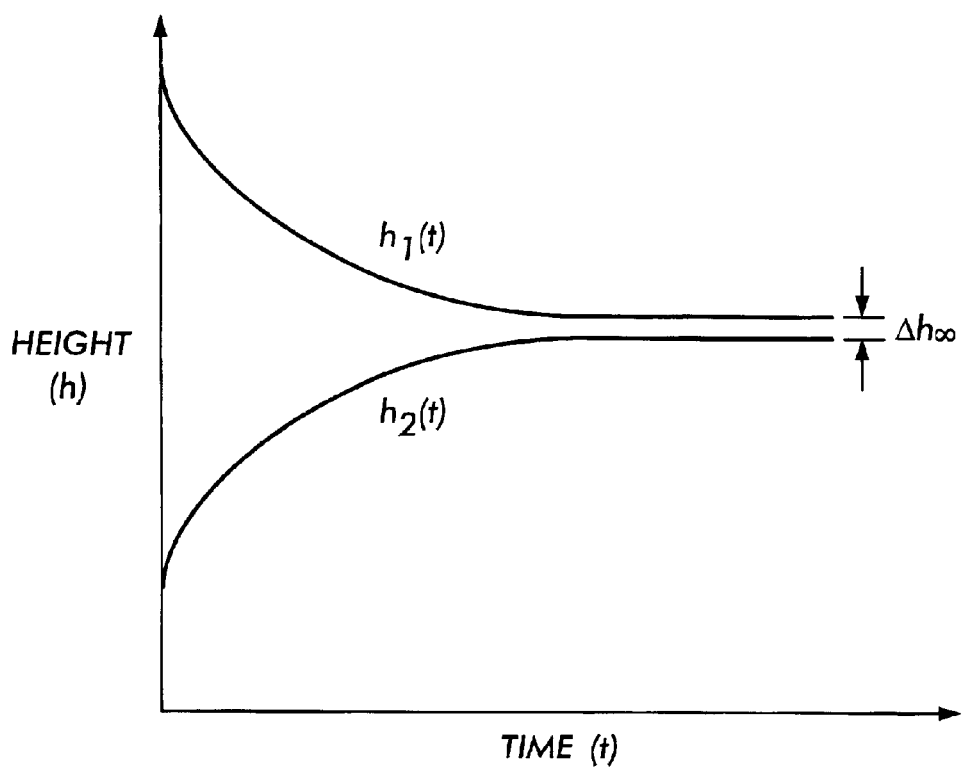
FIG. 2 is a graphical representation of the height of the respective columns of fluid over time in the two legs of the U-shaped tube.

Although any of the above-mentioned SCTVs can be used, the dual riser/single capillary viscometer (hereinafter "DRSC viscometer") is used by way of example only and is not limited to the DRSC viscometer 20. Thus, the entire disclosures of U.S. Pat. Nos. 6,322,524 and 6,402,703 (Kensey et al.) are incorporated by reference herein. FIG. 1 is a functional diagram of the DRSC viscometer 20 which basically comprises a pair of riser tubes R1 and R2 and a capillary tube 22 coupled between them (although it should be understood that the position of the capillary tube 22 is not limited to the position shown, but as discussed in U.S. Pat. No. 6,402,703 (Kensey et al.), can be located as part of either riser tube, etc.). During operation of the DRSC viscometer 20, a falling column of fluid 82 in the direction 83 is present as well as a rising column of fluid 84 in the direction 85 is present. At least one of these columns, preferably the rising column of fluid 84, is monitored by a column level detector 56 while a single data point of the falling column 82 is detected by a single point detector 954, it being understood that the falling column 82 may, alternatively, be monitored by a column level detector 54 (similar to detector 56). In any case, the data collected from the falling/rising columns 82/84 is conveyed to a computer for processing. FIG. 2 is a graphical representation of the height of the respective columns of fluid over time.

As mentioned earlier, the DRSC viscometer 20 is used by way of example only and that any of the other SCTVs could be used and wherein the data collected from those SCTVs may include the changing weight, volume, etc., of the fluid moving through the SCTVs. As a result, the phrase "fluid movement data" used throughout this Specification is not limited to the changing heights of the fluid columns 82/84 and can represent any data about the fluid movement through any of these SCTVs. Where "height vs. time" data is mentioned, it is done by way of example only.

Furthermore, as stated in U.S. Pat. No. 6,402,703 (Kensey et al.), there are a plurality of mathematical models that can be used as constitutive equations for the data obtained from the SCTVs, such as a power law model, a Casson model, a Carreau model, a Herschel-Bulkley model, a Powell-Eyring model, a Cross model, Carreau-Yasuda model. It is within the broadest scope of this invention to include all of these models. The following discussion utilizes a Casson model (physicians prefer a Casson model for physiological systems, although other models could be used) and is used by way of example only and not by way of limitation. Thus, one skilled in the art could substitute any of the above constitutive equation models for the exemplary Casson model that is discussed below.

It will be shown that using a Casson model (by way of example only), the following characteristic viscosity-shear rate relationship describes the viscosity of the fluid under test from approximately zero shear rate to approximately infinite shear rate:

$$V(t) = f_1 + \frac{f_2}{\sqrt{S(t)}} + \frac{f_3}{S(t)} \qquad \text{(equation 1)}$$

where V is the viscosity of the fluid under test, S is the shear rate and the coefficients $f_1$, $f_2$ and $f_3$ are derived from both (i) parameters of the DRSC viscometer and (ii) data collected from the DRSC viscometer 20 when a portion of the fluid under test is run through the DRSC viscometer 20. Once these coefficients are derived, the result is a viscosity-shear rate relationship or equation that describes the viscosity of that fluid in that system over all shear rates. Thus, for example, if the system is the circulatory system of a particular individual, once a portion of the circulating blood of that individual is diverted into the DRSC viscometer, data collected and the coefficients $f_1$, $f_2$ and $f_3$ derived, the result is a blood viscosity-shear relationship or equation unique to that individual. Knowing that relationship, a physician can then determine a particular viscosity at any location in the cardiovascular system of that individual by simply detecting the shear rate of the blood at that location and then plugging the shear rate value into the relationship. Moreover, the physician can now also determine the shear stress at that location by multiplying the viscosity of the fluid at that location with the shear rate at that location. Doing this at a plurality of locations, the physician can generate a shear stress profile of the entire cardiovascular system, a result heretofore unknown.

It should be understood that equation 1 is by way of example only and that if a different SCTV were used, e.g., the Single Capillary Tube Viscometer of application Ser. No. 09/908,374, the form of equation (1) would be different; similarly, if a different constitutive equation model were used, e.g., Herschel-Bulkley model, instead of the Casson model, the form of equation (1) may also be different. However, the concept is the same: using the method 120 of the present invention yields a viscosity-shear rate relationship over all shear rates unique to that system.

Figure 3:
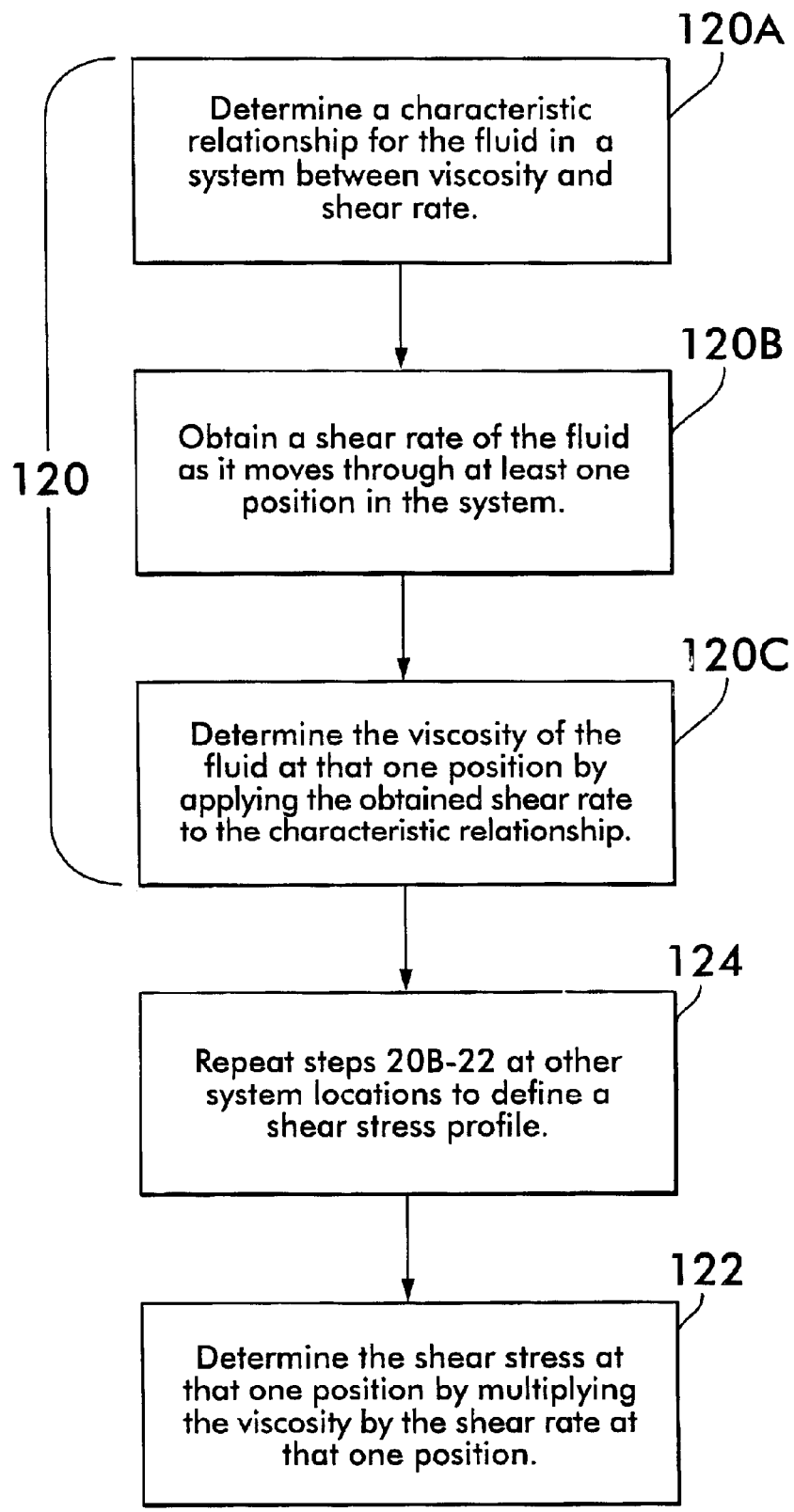
FIG. 3 is a flowchart of the method of the present invention.

As shown in FIG. 3, the method 120 of the present invention involves: determining a characteristic relationship for the fluid in a system between the viscosity an shear rate (120A); obtaining a shear rate of the fluid as it moves through at least one position in the system (120B); and determining the viscosity of the fluid at that one position as the fluid moves through that one position in the system by applying the shear rate to the characteristic relationship (120C). The first step 120A of determining the characteristic relationship will be discussed in detail later; suffice it to say that this relationship provides a viscosity-shear rate relationship for that particular fluid from approximately zero shear rate to infinite shear rate. The second step 120B of obtaining a shear rate can be accomplished by any well-known method of detecting the shear rate of a fluid, e.g., using ultrasonic devices, Doppler devices, NMR devices, MRI devices, etc. The third step 120C applies the detected shear rate to the characteristic equation from step 120A to arrive at the particular viscosity for the fluid at the particular location where the shear rate was detected. This method 120 can be supplemented by determining the shear stress at that one position by multiplying the determined viscosity by the detected shear rate (step 122). Furthermore, by repeating steps 120B–122 a shear stress profile can be determined for the fluid flowing in the system (step 124).

As mentioned earlier, step 120A involves determining the characteristic viscosity-shear rate relationship for the particular fluid. The following discussion describes the determination of equation 1, bearing in mind that the Casson model is used by way of example only and using the DRSC viscometer 20, also by way of example only.

Figure 4:
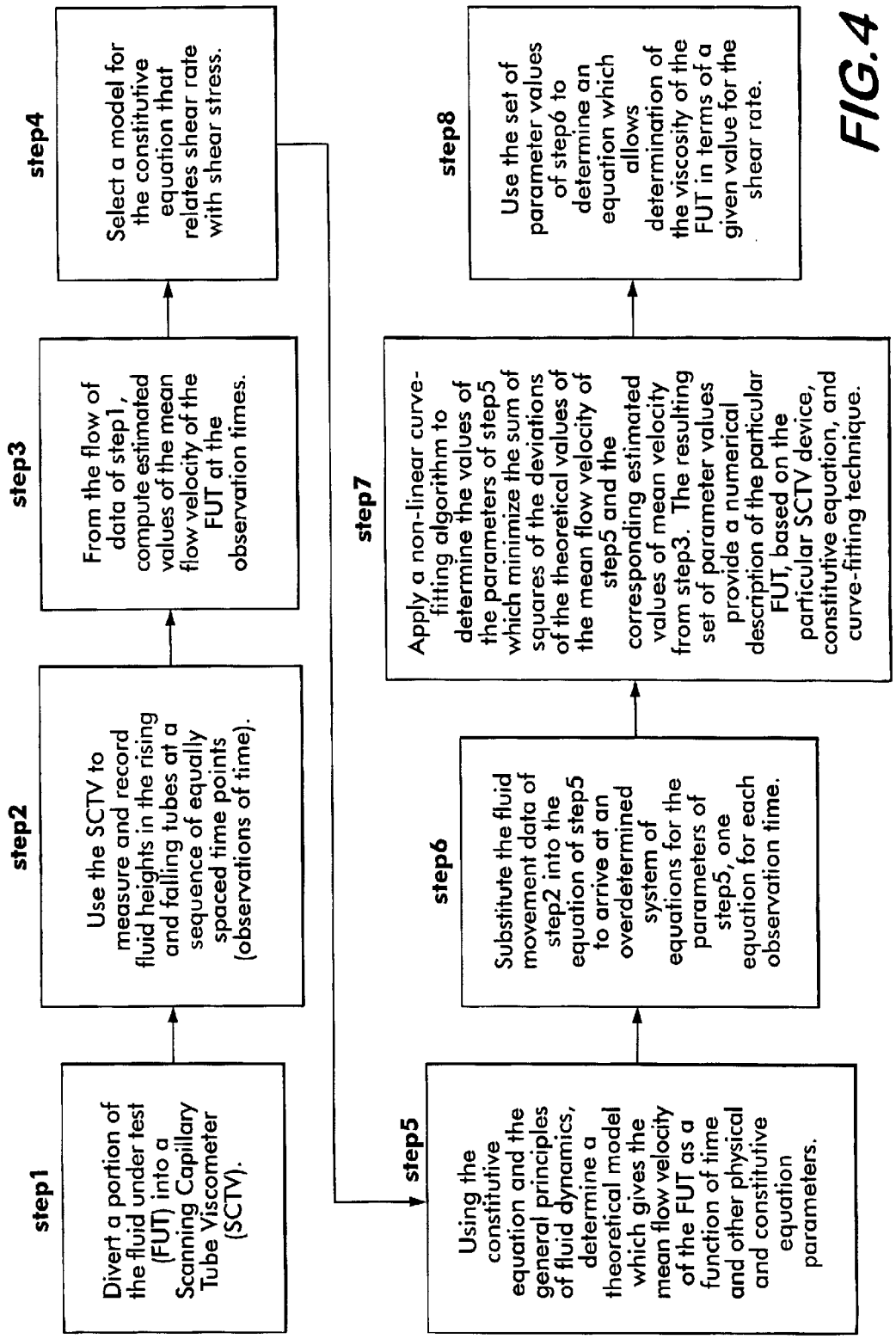
FIG. 4 is a flowchart of the method of determining the fluid's characteristic viscosity-shear rate relationship.

As shown in FIG. 4, the method of determining the fluid's characteristic viscosity-shear rate relationship includes the following steps:

step1) Divert a portion of the fluid under test (FUT) into a Scanning Capillary Tube Viscometer (SCTV);

step2) Use the SCTV to measure and record fluid movement data (e.g., fluid heights in the rising and falling tubes, changing weight, volume, etc.) at a sequence of equally spaced time points (observations of time);

step3) From the flow of data of step1, compute estimated values of the mean velocity of the FUT at the observation times;

step4) Select a model for the constitutive equation that relates shear rate with shear stress.

step5) Using the constitutive equation and the general principles of fluid dynamics, determine a theoretical model which gives the mean flow velocity of the FUT as a function of time and other physical and constitutive equation parameters;

step6) Substitute the fluid movement data of step2 into the equation of step5 to arrive at an overdetermined system of equations for the parameters of step5, one equation for each observation time. A typical equation expresses the theoretical value of the mean velocity corresponding to a single observation time in terms of the unknown parameter values;

step7) Apply a non-linear curve-fitting algorithm to determine the values of the parameters of step5 which minimize the sum of squares of the deviations of the theoretical values of the mean velocity of step5 and the corresponding estimated values of mean velocity from step3. The resulting set of parameter values provide a numerical description of the particular FUT, based on the particular SCTV device, constitutive equation, and curve-fitting technique;

step8) Use the set of parameter values of step6 to determine an equation which allows determination of the viscosity of the FUT in terms of a given value for the shear rate.

Derivation of Equation 1

The following explains the theory underlying the algorithm for calculating the relationship between shear rate and viscosity as implemented using a SCTV (e.g., DRSC viscometer 20) and its associated software, it being remembered that the DRSC viscometer 20 is used by way of example only and that any of the other SCTVs could be used. In the DRSC viscometer 20, this algorithm is currently implemented as both an Excel-based VB-macro and as a C++ OCX.

As discussed earlier, the DRSC viscometer 20 comprises two identical riser tubes connected by a capillary tube 22 of significantly smaller diameter. A falling column of fluid 82 is present in riser tube R1 and a rising column of fluid 84 is present in the other riser tube R2. During the period before equilibrium is achieved, the heights of the fluid columns are measured at equal time intervals of length $\Delta t=0.02$ seconds. Using the algorithm described herein, the shear rate and viscosity are estimated at the endpoints of the various time intervals. If S denotes the shear rate and V denotes the viscosity, then both are functions of time, as given by the following parametric equations:

$$S=S(t)$$

$$V=V(t)$$

Figure 5:
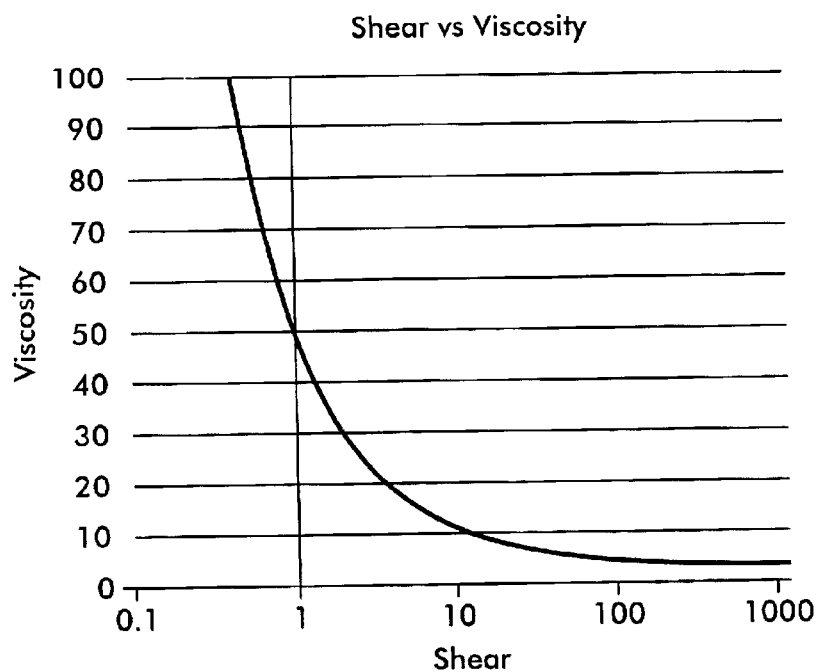
FIG. 5 depicts a typical functional relationship between shear rate and viscosity.

The viscosity is a decreasing function of the shear rate, so that, ideally, the parameter t may be eliminated and viscosity described as a function of shear rate:

$$V=F(S)$$

for an appropriate function F. A typical functional relationship between shear rate and viscosity is shown in FIG. 5.

It is the purpose of the shear rate-viscosity algorithm to compute the functional relationship between shear and viscosity as well as to compute additional parameters describing the fluid flow through the capillary tube 22 during the test period. As part of the algorithm, noise is filtered from the observed data.

In the remainder of this section, the following notations are used:

g=gravitational acceleration;
$\rho$=the density of the fluid under test;
$R_c$=the radius of the capillary tube 22;
L=the length of the capillary tube 22;
y(t)=the mean flow velocity at the riser tubes R1/R2;
$R_r$=the (common) radius of the riser tubes R1/R2;
$x_1(t)$=the height of the falling tube in mm at time t
$x_2(t)$=the height of the riser tube in mm at time t It is assumed throughout that blood flows in accordance with the Casson model, which is described in detail below. From experimental observations obtained using the DRSC viscometer 20, at low shear rates (e.g., $<10$ $s^{-1}$) and corresponding low velocity, the flow of blood in the viscometer no longer conforms to the Casson model. To accommodate this observation, a "quasi-Casson" model can be proposed which more accurately describes the flow at low shear. This model produces very repeatable results with viscosities accurate to within approximately ±3% for shear rates from 1 to 300.

The Casson Model

In this Section, elementary facts about the Casson model are discussed, notations are set for what follows, and the time-velocity formula for blood flow in the DRSC viscometer 20 is derived. The basic reference for the Casson model is Fung, Y. C., Biomechanics-Mechanical Properties of Living Tissues, $2^{nd}$ edition, Springer-Verlag, N.Y., 1993, pp. 76–82. With the capillary tube 22 length oriented along the x-axis (i.e., horizontally, as shown in FIG. 1), the blood flow through the capillary tube 22 is left to right. Polar coordinates are chosen, with the radial variable measuring the radius of the capillary tube 22. It is assumed that blood is flowing in the positive direction along the capillary tube 22, i.e., left to right. It is also assumed that the blood flow is laminar and that there are no end effects. Assume $$\frac{dp}{dx}$$

denotes the pressure gradient along the capillary tube 22. Consider a cylinder of length L at radius r in the capillary. Then the pressure gradient corresponds to a total pressure $$L \cdot \left(-\frac{dp}{dx}\right)$$

acting on an area of $\pi r^2$, for a total force of $$-\pi r^2 L \frac{dp}{dx}.$$

On the other hand, the shear stress acting on this cylinder is denoted by $\tau$. Then this stress acts on an area $2\pi r$, corresponding to a force of $2\pi r \tau$. Assuming laminar flow, there is no acceleration of the fluid and the forces must be in balance, so that:

$$2\pi r \tau = -\pi r^2 L \frac{dp}{dx}$$

Solving for $\tau$ gives Stokes' equation for the capillary tube 22.

$$\tau = -\frac{r}{2L}\frac{dp}{dx} \tag{2-1}$$

Now, a formula for $$\frac{dp}{dx}$$

in the specific case of the capillary tube 22 is derived. Let $p_1$ and $p_2$ denote the pressures at the top of the falling and rising fluid columns 82/84, respectively, at time t, and let $x_1(t)$ and $x_2(t)$ denote the heights of those tubes at time t. Furthermore, let $v_1, v_2$ denote the velocities at the tops of the two fluid columns, $\rho$ the density of blood, and g the acceleration due to gravity. Finally, let $\Delta h_{st}$ be the additional height of the rising fluid column 84 due to surface tension. (In the rising fluid column 84, there is no wetting, whereas the falling fluid column 82 has complete wetting.) Then Pascal's theorem gives:

$$p_1 + \frac{1}{2}\rho v_1^2 + \rho g x_1(t) = p_2 + \frac{1}{2}\rho v_2^2 + \rho g x_2(t) - \frac{dp}{dx} + \rho g \Delta h_{st}$$

Since $p_1$ and $p_2$ are both equal to atmospheric pressure and since $v_1 = v_2$ by incompressibility, we see that:

$$-\frac{dp}{dx} = \rho g[x_1(t) - x_2(t) - \Delta h_{st}] \tag{2-2}$$

In what follows, it will be convenient to write $a_1$ in place of $\Delta h_{st}$ to set $$\Delta = x_1(t) - x_2(t) - \Delta h_{st} = x_1(t) - x_2(t) - a_1$$

In terms of this notation, then:

$$-\frac{dp}{dx} = \rho g \Delta \tag{2-3}$$

Combining equations (2-1) and (2-3) gives:

$$\tau = \frac{\rho g r \Delta}{2L} \tag{2-4}$$

Since the flow through the capillary tube 22 is axisymmetric, the velocity u is a function of r alone, u=u(r). The shear rate $\dot{\gamma}$ is then defined by the equation:

$$\dot{\gamma} = -\frac{du}{dr} \tag{2-5}$$

The shear rate and the shear stress are now related using the constitutive model, namely, the Casson model (by way of example only):

$$\sqrt{\tau} = \begin{cases} \sqrt{\tau_y} + \sqrt{a_3 \dot{\gamma}} & \text{for } \tau \geq \tau_y \\ 0 \text{ and } \dot{\gamma} = 0 & \text{for } 0 \leq \tau < \tau_y \end{cases} \tag{2-6}$$

where $\tau_y$ and $a_3$ are constants. The parameter $\tau_y$ is called the yield stress and will be discussed shortly. It should be noted that $\tau$ is a function of r and t and that:

$$\dot{\gamma} = -\frac{du}{dr} = \begin{cases} \frac{1}{a_3}\left(\sqrt{\tau} - \sqrt{\tau_y}\right)^2 & \text{for } \tau \geq \tau_y \\ 0 & \text{for } 0 \leq \tau < \tau_y \end{cases} \tag{2-7}$$

Let $R_c$ denote the radius of the capillary tube 22. As mentioned above, the shear stress $\tau$ is a function of r (and t). When $r=R_c$, the location at the wall of the capillary tube 22, the value of the shear stress is called the wall stress. Set $$\tau_y = \frac{\rho g R_c}{2L} a_2$$

for a suitable constant $a_2$. Inserting the value of $\tau$ from equation (2-4) gives:

$$\dot{\gamma} = -\frac{du}{dr} = \begin{cases} \frac{\rho g}{2L a_3}\left(\sqrt{\Delta r} - \sqrt{a_2 R_c}\right)^2 & \text{for } \tau \geq \tau_y \\ 0 & \text{for } 0 \leq \tau < \tau_y \end{cases} \tag{2-8}$$

In particular, for $r=R_c$, then:

$$\dot{\gamma}(R_c) = \frac{\rho g R_c}{2La_3}(\sqrt{\Delta} - \sqrt{a_2})^2 \qquad (2\text{-}9)$$

The viscosity $\eta$ is defined as the ratio of shear stress to shear rate, calculated at the wall of the capillary tube 22:

$$\eta = \frac{\tau(R_c)}{\dot{\gamma}(R_c)} \qquad (2\text{-}10)$$

Thus, from equations (2-4), (2-9), and (2-10):

$$\eta = \frac{\rho g R_c \Delta}{2L} \cdot \frac{2La_3}{\rho g R_c (\sqrt{\Delta} - \sqrt{a_2})^2} \qquad (2\text{-}11)$$

$$= \frac{a_3 \Delta}{(\sqrt{\Delta} - \sqrt{a_2})^2}$$

The velocity profile for flow through the capillary tube 22 and through the riser tubes R1/R2 is now derived. Introduce the variable $$r_1 = R_c a_2/\Delta.$$

Then by equation (2-5), the condition $\tau \geq \tau_y$ is equivalent to $$r \geq r_1$$

so that equation (2-9) may be written in the form:

$$\dot{\gamma} = -\frac{du}{dr} = \begin{cases} \frac{\rho g \Delta}{2La_3}(\sqrt{r} - \sqrt{r_1})^2 & \text{for } r \geq r_1 \\ 0 & \text{for } 0 \leq r < r_1 \end{cases} \qquad (2\text{-}12)$$

Integrating this last equation with respect to r:

$$u(r) - u(R_c) = \int_r^{R_c} \frac{\rho g \Delta}{2La_3}(r + r_1 - 2\sqrt{r_1}\, r^{1/2}) dr$$

$$= \frac{\rho g \Delta}{2La_3}\left(\frac{1}{2}r^2 + r_1 r - \frac{4}{3}\sqrt{r_1}\, r^{3/2}\right)\bigg|_r^{R_c}$$

$$= \frac{\rho g \Delta}{2La_3}\left(\frac{1}{2}[R_c^2 - r^2] + r_1[R_c - r] - \frac{4}{3}\sqrt{r_1}\,[R_c^{3/2} - r^{3/2}]\right)$$

where the last formula is valid for $r_1 \leq r \leq R_c$. Noting the boundary condition $u(R_c)=0$, and applying the second half of equation 2-12, the last equation may be written in the form:

$$u(r) = \qquad (2\text{-}13)$$

$$\frac{\rho g \Delta}{4La_3}\left([R_c^2 - r^2] + 2r_1[R_c - r] - \frac{8}{3}\sqrt{r_1}\,[R_c^{3/2} - r^{3/2}]\right)(r_1 \leq r \leq R_c)$$

Since the velocity $u(r)$ is constant, equal to the core velocity for $0 \leq r \leq r_1$, setting $r=r_1$ in the last equation yields:

$$u(r) = \frac{\rho g \Delta}{4La_3}\left(R_c^2 - \frac{1}{3}r_1^2 + 2r_1 R_c - \frac{8}{3}\sqrt{r_1}\, R_c^{3/2}\right)(0 \leq r \leq r_1) \qquad (2\text{-}14)$$

The volume flow rate through the capillary tube 22 can be determined by integrating the velocity function times the area of an annulus of the capillary tube 22 of radius r:

$$\dot{Q} = \int_0^{R_c} 2\pi r u(r) dr \qquad (2\text{-}15)$$

Thus, $$\dot{Q} = \dot{Q}_1 + \dot{Q}_2$$

where $$\dot{Q}_1 = \int_0^{r_1} 2\pi r u(r) dr$$

$$\dot{Q}_2 = \int_{r_1}^{R_c} 2\pi r u(r) dr$$

Applying formulas (2-14) and (2-15), yields:

$$\dot{Q}_1 = \int_0^{r_1} 2\pi r \left[\frac{\rho g \Delta}{4La_3}\left(R_c^2 - \frac{1}{3}r_1^2 + 2r_1 R_c - \frac{8}{3}\sqrt{r_1}\, R_c^{3/2}\right)\right] dr \qquad (2\text{-}16)$$

$$= \frac{\pi \rho g \Delta}{2La_3}\left(R_c^2 - \frac{1}{3}r_1^2 + 2r_1 R_c - \frac{8}{3}r_1^{1/2} R_c^{3/2}\right)\int_0^{r_1} r\, dr$$

$$= \frac{\pi \rho g \Delta}{2La_3}\left(R_c^2 - \frac{1}{3}r_1^2 + 2r_1 R_c - \frac{8}{3}r_1^{1/2} R_c^{3/2}\right)\frac{r_1^2}{2}$$

$$= \frac{\pi \rho g \Delta}{2La_3}\left(R_c^2 r_1^2 - \frac{1}{3}r_1^4 + 2r_1^3 R_c - \frac{8}{3}r_1^{5/2} R_c^{3/2}\right)$$

$$\dot{Q}_2 = \int_{r_1}^{R_c} 2\pi r \left[\frac{\rho g \Delta}{4La_3}\left(\begin{array}{c}[R_c^2 - r^2] + 2r_1[R_c - r] - \\ \frac{8}{3}\sqrt{r_1}\,[R_c^{3/2} - r^{3/2}]\end{array}\right)\right] dr \qquad (2\text{-}17)$$

$$= \frac{\pi \rho g \Delta}{2La_3}\int_{r_1}^{R_c}\left(\begin{array}{c}R_c^2 r - r^3 + 2r_1 R_c r - 2r_1 r^2 - \\ \frac{8}{3}\sqrt{r_1}\, R_c^{3/2} r + \frac{8}{3}\sqrt{r_1}\, r^{5/2}\end{array}\right) dr$$

$$= \frac{\pi \rho g \Delta}{2La_3}\begin{bmatrix}\frac{1}{2}R_c^2(R_c^2 - r_1^2) - \left(\frac{1}{4}R_c^4 - \frac{1}{4}r_1^4\right) + \\ r_1 R_c(R_c^2 - r_1^2) - \frac{2}{3}r_1 R_c^3 + \frac{2}{3}r_1^4 - \\ \frac{4}{3}\sqrt{r_1}\, R_c^{3/2}(R_c^2 - r_1^2) + \frac{16}{21}\sqrt{r_1}\,(R_c^{7/2} - r_1^{7/2})\end{bmatrix}$$

$$= \frac{\pi \rho g \Delta}{2La_3}\begin{bmatrix}\frac{1}{2}R_c^4 - \frac{1}{2}R_c^2 r_1^2 - \frac{1}{4}R_c^4 + \frac{1}{4}r_1^4 + \\ R_c^3 r_1 - R_c r_1^3 - \frac{2}{3}R_c^3 r_1 + \frac{2}{3}r_1^4 - \\ \frac{4}{3}R_c^{7/2} r_1^{1/2} + \frac{4}{3}R_c^{3/2} r_1^{5/2} + \frac{16}{21}R_c^{7/2} r_1^{1/2} - \frac{16}{21}r_1^4\end{bmatrix}$$

$$= \frac{\pi \rho g \Delta}{2La_3}\begin{bmatrix}\frac{1}{4}R_c^4 + r_1\left(R_c^3 - \frac{2}{3}R_c^3\right) + r_1^2\left(-\frac{1}{2}R_c^2\right) + \\ r_1^3(-R_c) + r_1^4\left(\frac{1}{4} + \frac{2}{3} - \frac{16}{21}\right) + \\ r_1^{1/2}\left(-\frac{4}{3}R_c^{7/2} + \frac{16}{21}R_c^{7/2}\right) + r_1^{5/2}\left(\frac{4}{3}R_c^{3/2}\right)\end{bmatrix}$$

Therefore, $$\dot{Q} = \frac{\pi \rho g \Delta}{2La_3}\begin{bmatrix}\frac{1}{4}R_c^4 + r_1\left(R_c^3 - \frac{2}{3}R_c^3\right) + r_1^2\left(-\frac{1}{2}R_c^2 + \frac{1}{2}R_c^2\right) + \\ r_1^3(-R_c + R_c) + r_1^4\left(\frac{1}{4} + \frac{2}{3} - \frac{16}{21} - \frac{1}{6}\right) + \\ r_1^{1/2}\left(-\frac{4}{3}R_c^{7/2} + \frac{16}{21}R_c^{7/2}\right) + r_1^{5/2}\left(\frac{4}{3}R_c^{3/2} - \frac{4}{3}R_c^{3/2}\right)\end{bmatrix} \qquad (2\text{-}18)$$

$$= \frac{\pi \rho g \Delta}{2La_3}\left[\frac{1}{4}R_c^4 + \frac{1}{3}r_1 R_c^3 - \frac{1}{84}r_1^4 + \frac{4}{7}r_1^{1/2} R_c^{7/2}\right]$$

$$= \frac{\pi \rho g \Delta}{8La_3}\left[R_c^4 + \frac{4}{3}r_1 R_c^3 - \frac{1}{21}r_1^4 - \frac{16}{7}r_1^{1/2} R_c^{7/2}\right]$$

And since $r_1 = R_c a_2/\Delta$, the last expression may be written in the form:

$$\dot{Q} = \frac{\pi \rho g \Delta}{8La_3}\left[R_c^4 + \frac{4}{3}\left(\frac{R_c a_2}{\Delta}\right)R_c^3 - \frac{1}{21}\left(\frac{R_c a_2}{\Delta}\right)^4 - \frac{16}{7}\left(\frac{R_c a_2}{\Delta}\right)^{1/2}R_c^{7/2}\right] \quad (2\text{-}19)$$

$$= \frac{\pi \rho g \Delta R_c^4}{8La_3}\left[1 + \frac{4}{3}\frac{a_2}{\Delta} - \frac{1}{21}\left(\frac{a_2}{\Delta}\right)^4 - \frac{16}{7}\left(\frac{a_2}{\Delta}\right)^{1/2}\right]$$

Let $y(t)$ denote the mean velocity of the blood at either of the riser tubes R1/R2 and let $R_r$ denote the radius of one of these tubes R1/R2. Then the cross-sectional area of a riser tube is $\pi R_r^2$ so that $$\pi R_r^2 y(t) = \dot{Q}$$

so that by equation (2-19), the following result is:

$$y(t) = \frac{\rho g \Delta R_c^4}{8R_r^2 La_3}\left[1 + \frac{4}{3}\frac{a_2}{\Delta} - \frac{1}{21}\left(\frac{a_2}{\Delta}\right)^4 - \frac{16}{7}\left(\frac{a_2}{\Delta}\right)^{1/2}\right] \quad (2\text{-}20)$$

Equations (2-19) and (2-20) are the standard results of the Casson model, expressed in a more convenient form. If should be understood that the above equation was derived assuming that the variable t is fixed. Actually, the only dependence on time is in the variable $\Delta = x_1(t) - x_2(t) - a_1$. In particular, the entire derivation applies if the falling fluid column 82 is subject to a pressure which varies with time, such as a pulsatile pressure (as long as the heights $x_1(t)$ and $x_2(t)$ reflect the effect of that pressure).

In what follows it is convenient to have equation (2-20) in a slightly different form. Define the constant c which depends only on physical constants and the geometry of the DRSC viscometer 20, as follows:

$$c = \frac{\rho g R_c^4}{8R_r^2 L} \quad (2\text{-}21)$$

Then insert this definition as well as the definition of $\Delta$ into equation (2-20) to obtain:

$$y(t) = \frac{c}{a_3}\left[(x_1 - x_2 - a_1) + \frac{4}{3}a_2 - \frac{16}{7}\sqrt{a_2(x_1 - x_2 - a_1)} - \frac{a_2^4}{21(x_1 - x_2 - a_1)^3}\right] \quad (2\text{-}22)$$

Equation (2-20) may be written in a form which lays out the relationship between velocity $y(t)$ and the shear rate $\dot{\gamma}$. From equation (2-4):

$$\frac{a_2}{\Delta} = \frac{c_1}{\tau} \quad (2\text{-}23)$$

where now $\tau$ refers to the shear at the wall of the capillary ($\tau = \tau_w$) and where the new constant is introduced:

$$c_1 = \frac{\rho g R_c a_2}{2L}. \quad (2\text{-}24)$$

Therefore, equation (2-20) may be written in the form:

$$y(t) = \frac{\rho g \Delta R_c^4}{8R_r^2 La_3}\left[1 + \frac{4}{3}\frac{a_2}{\Delta} - \frac{1}{21}\left(\frac{a_2}{\Delta}\right)^4 - \frac{16}{7}\left(\frac{a_2}{\Delta}\right)^{1/2}\right] \quad (2\text{-}25)$$

$$= \frac{c}{a_3}\left[a_2\left(\frac{a_2}{\Delta}\right)^{-1} + \frac{4}{3}a_2 - \frac{a_2}{21}\left(\frac{a_2}{\Delta}\right)^3 - \frac{16a_2}{7}\left(\frac{a_2}{\Delta}\right)^{-1/2}\right]$$

$$= \frac{ca_2}{a_3}\left[\left(\frac{c_1}{\tau}\right)^{-1} + \frac{4}{3} - \frac{1}{21}\left(\frac{c_1}{\tau}\right)^3 - \frac{16}{7}\left(\frac{c_1}{\tau}\right)^{-1/2}\right]$$

Using this last equation for a given velocity value y, the corresponding shear stress $\tau$ may be determined. Then, using equation (2-8), the corresponding shear rate $\dot{\gamma}$ may be determined:

$$\dot{\gamma} = \frac{1}{a_3}\left(\sqrt{\tau} - \sqrt{\tau_3}\right)^2 \quad (2\text{-}26)$$

$$= \frac{1}{a_3}\left(\sqrt{\tau} - \sqrt{\frac{\rho g R_c}{2L}a_2}\right)^2$$

$$= \frac{1}{a_3}\left(\sqrt{\tau} - \sqrt{c_1}\right)^2$$

In this way, the shear rate S can be expressed as a function $S(y)$ of the velocity. Furthermore, the quantities $a_1, a_2, a_3$ are constant and, in particular, do not depend on t.

The Relationship Between Shear Rate and Viscosity

In this section, several formulas are defined which are at the heart of the shear-viscosity model of the present invention. Specifically, it is shown that shear rate and viscosity are related by a formula of the type:

$$V = f_1 + \frac{f_2}{S} + \frac{f_3}{\sqrt{S}}$$

where $f_1, f_2, f_3$ are constants. This implies, among other things, that the graph of viscosity vs. shear rate always has the same general shape as the graph shown in FIG. 5. This had been confirmed in many instances, based on experimental data. However, in this section, it is shown that the above relationship between shear rate and viscosity is a consequence of the Casson model.

Starting with equation (2-9):

$$S(t) = \dot{y}(R_c) = \frac{\rho g R_c}{2La_3}\left(\sqrt{\Delta} - \sqrt{a_2}\right)^2$$

Solve the equation for the fundamental expression $\Delta = x_1(t) - x_2(t) - a_1$:

$$\sqrt{S} = \sqrt{\frac{\rho g R_c}{2a_3 L}}\left(\sqrt{\Delta} - \sqrt{a_2}\right)$$

$$\left(\sqrt{\frac{2a_3 SL}{\rho g R_c}} + \sqrt{a_2}\right)^2 = \Delta$$

Next, consider the equation (2.11) for viscosity:

$$V(t) = \eta = \frac{a_3 \Delta}{\left(\sqrt{\Delta} - \sqrt{a_2}\right)^2}$$

Now substitute the expression for $\Delta$ into the last equation:

$$V(t) = \frac{a_3 \left(\sqrt{\frac{2a_3 SL}{\rho g R_c}} + \sqrt{a_2}\right)^2}{\left[\left(\sqrt{\frac{2a_3 SL}{\rho g R_c}} + \sqrt{a_2}\right) - \sqrt{a_2}\right]^2}$$

$$= \frac{\rho g R_c}{2LS}\left(\frac{2a_3 SL}{\rho g R_c} + a_2 + 2\sqrt{\frac{2a_3 a_2 SL}{\rho g R_c}}\right)$$

$$= f_1 + \frac{f_2}{S} + \frac{f_3}{\sqrt{S}}$$

where $$f_1 = a_3$$

$$f_1 = a_3$$

$$f_2 = \frac{a_2 \rho g R_c}{2L}$$

$$f_3 = \sqrt{\frac{2\rho g R_c a_2 a_3}{L}}$$

Thus, the relationship between shear rate S and viscosity V is given by the equation:

$$V = f_1 + \frac{f_2}{S} + \frac{f_3}{\sqrt{S}} \qquad \text{(equation 1)}$$

where the coefficients $f_1, f_2, f_3$ are derived from the curve fitting constants and are given by:

$$f_1 = a_3 \qquad (1\text{-}2)$$

$$f_2 = \frac{a_2 \rho g R}{2L}$$

$$f_3 = \sqrt{\frac{2\rho g R a_2 a_3}{L}}$$

Other examples of this application include hydraulic fluid systems, engine oil systems. As mentioned earlier, the viscosity equation represents the viscosity-shear rate relationship for a fluid flowing through a system (e.g., blood in the body; hydraulic fluid in a control system, oil in engine system, etc.). Therefore, to find the viscosity (or shear stress) of that fluid at any point in the system, one need only detect the shear rate at that point and then plug the shear rate into the equation.

Where the system is the cardiovascular system of a living being and the fluid is the circulating blood of the living being, although equation 1 gives the value of the viscosity for any shear rate, it does not describe what shear rates are actually being attained within an actual artery or the relative durations of such viscosities. Thus, the following discussion addresses these issues.

In particular, in a cardiac cycle, which is assumed to be of duration $T_0$, the variable t measures time within this cycle; $\eta(t)$ denotes the viscosity in a specified artery at time t and $\eta_{ave}$ denotes the time average of $\eta(t)$ over the cardiac cycle. The variable $\eta(t)$ is known as the "cyclic rheological profile" and $\eta_{ave}$ is known as the "average cyclic viscosity" (ACV) of the artery. These same notations and terminology may be applied to the capillary tube 22 in the DRSC viscometer 20, where the capillary tube 22 represents a virtual artery. It will be shown how to use equation 1 to compute $\eta(t)$ and $\eta_{ave}$. Furthermore, it will be shown how to connect the cyclic rheological profile and the ACV for a capillary tube 22 to an actual artery.

To explain the significance of these results, the equation (1) provides a relationship between shear rate S and viscosity V. This relationship may be plotted consisting of the points (S,V) for every possible shear rate S. (See FIG. 6.) The curve is subject-dependent and gives a complete rheological profile of the subject (that is, it gives the viscosity at at all shear rates). However, this rheological profile does not give any information about what viscosities are actually achieved in the subject's arteries and the proportion of time spent at each viscosity. That is precisely the information provided by the functions $\eta(t)$ and $\dot{\gamma}(t)$.

Figure 7:
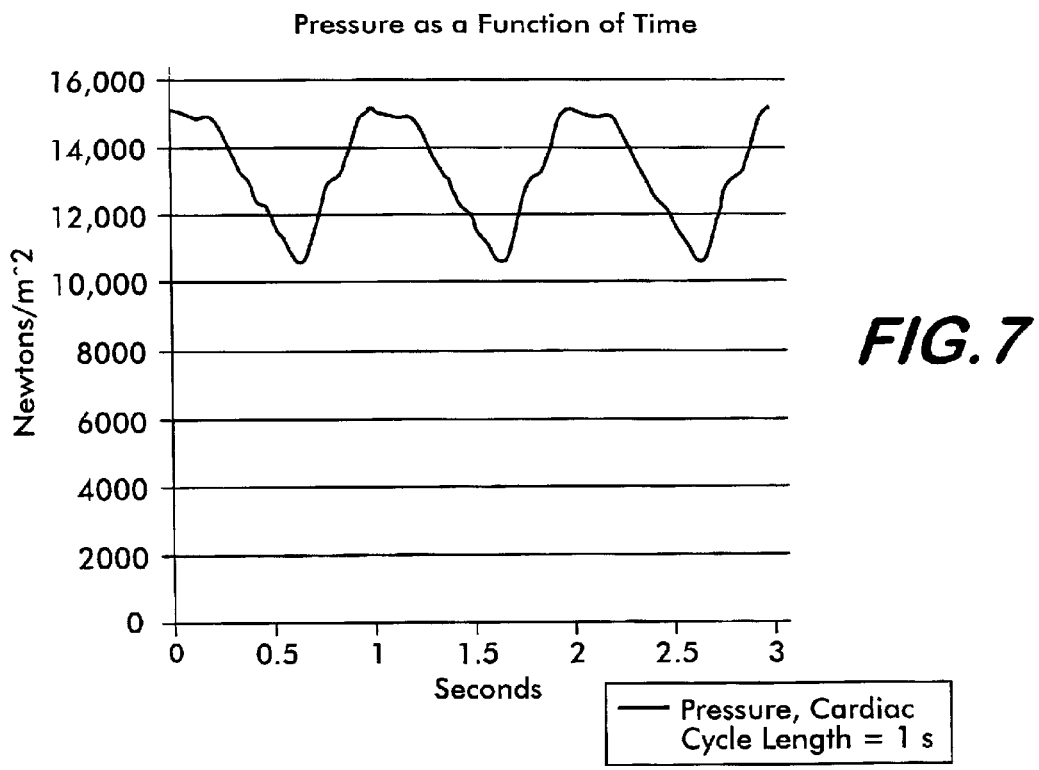
FIG. 7 is a graphical depiction of the pressure in the artery as a function of time.
Figure 8:
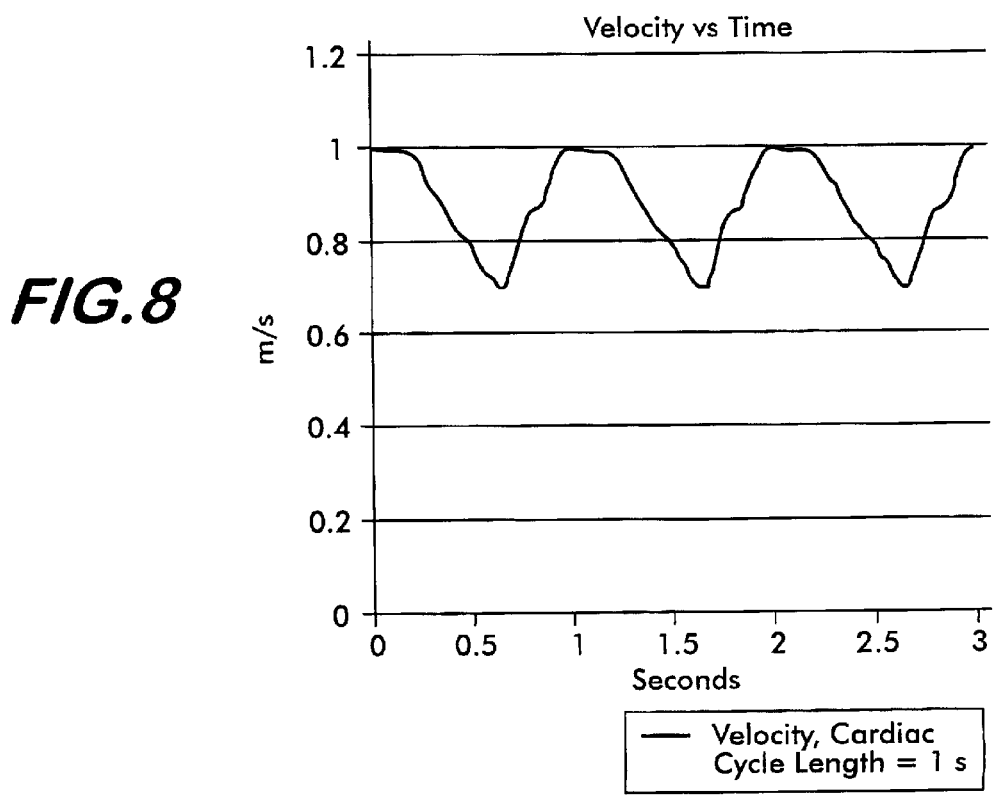
FIG. 8 is a graphical depiction of the flow rate in the artery, computed using a Windkessel model.
Figure 9:
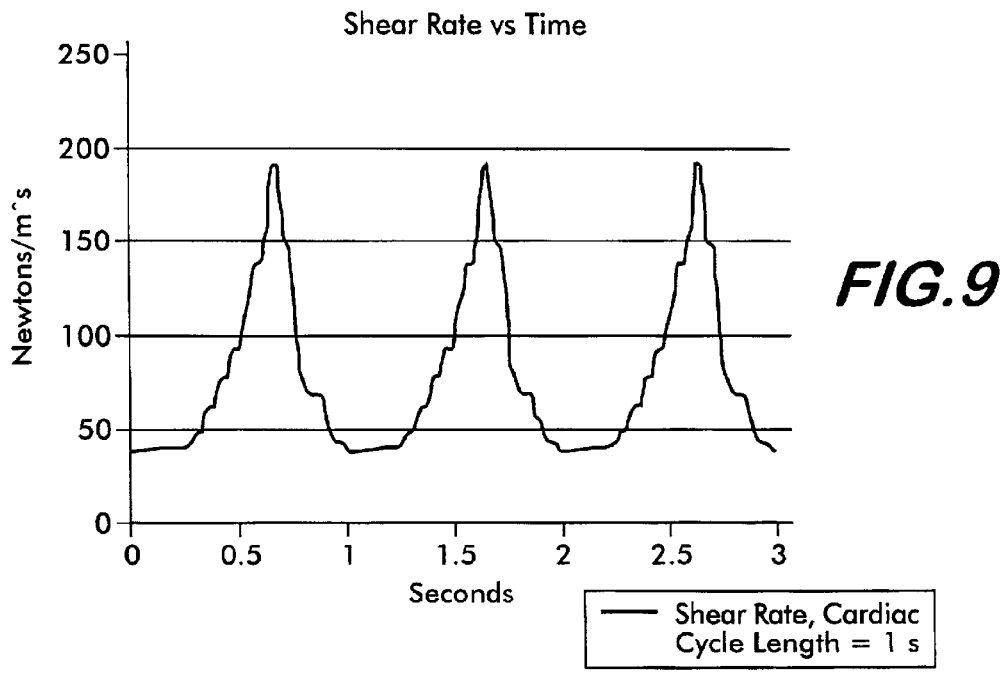
FIG. 9 is a graphical depiction of the shear rate function.
Figure 10:
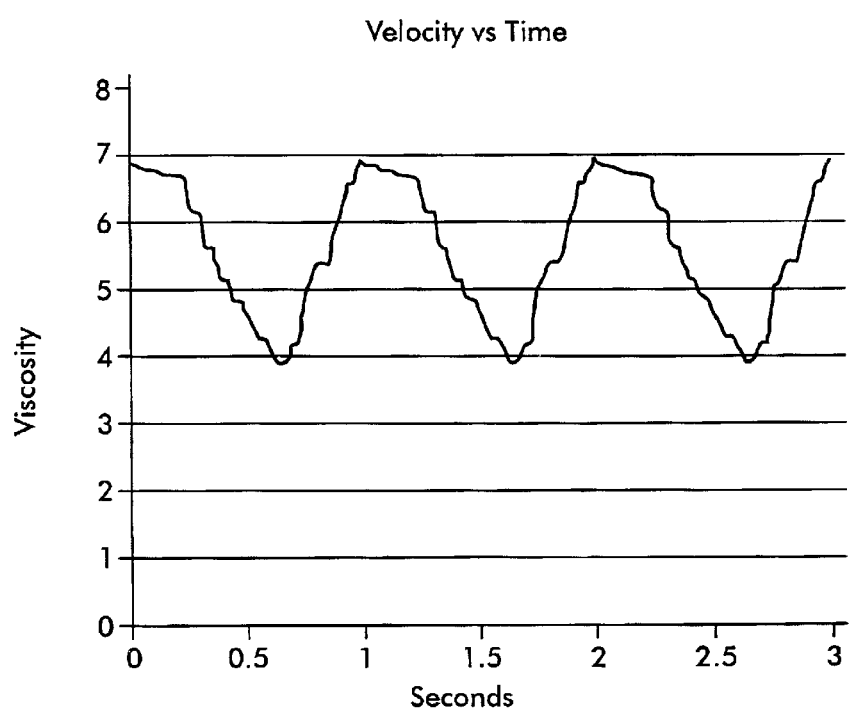
FIG. 10 is a graphical depiction of the viscosity function.

The following discussion provides an example of these functions. Assume an artery whose pulse-pressure information is given in FIG. 7. The length of each cardiac cycle is 1 second. Assuming, by way of example only, the following physical characteristics of the artery and the blood flow in it are:

Length=0.1 m
Radius at systole=0.007 m
Radius at diastole=0.0035 m
Flow rate at systole=1 m/s
Flow rate at diastole=0.7 m/s
(These numbers are for purposes of illustration only and do not represent the data for an actual subject.) A model based on the classic Windkessel flow model is used to compute the flow rate as a function of time. The result is given in FIG. 8. The main result of methodology is to provide a technique to calculate the shear rate and viscosity as a function of time, as shown in FIGS. 9 and 10, respectively.

Figure 6:
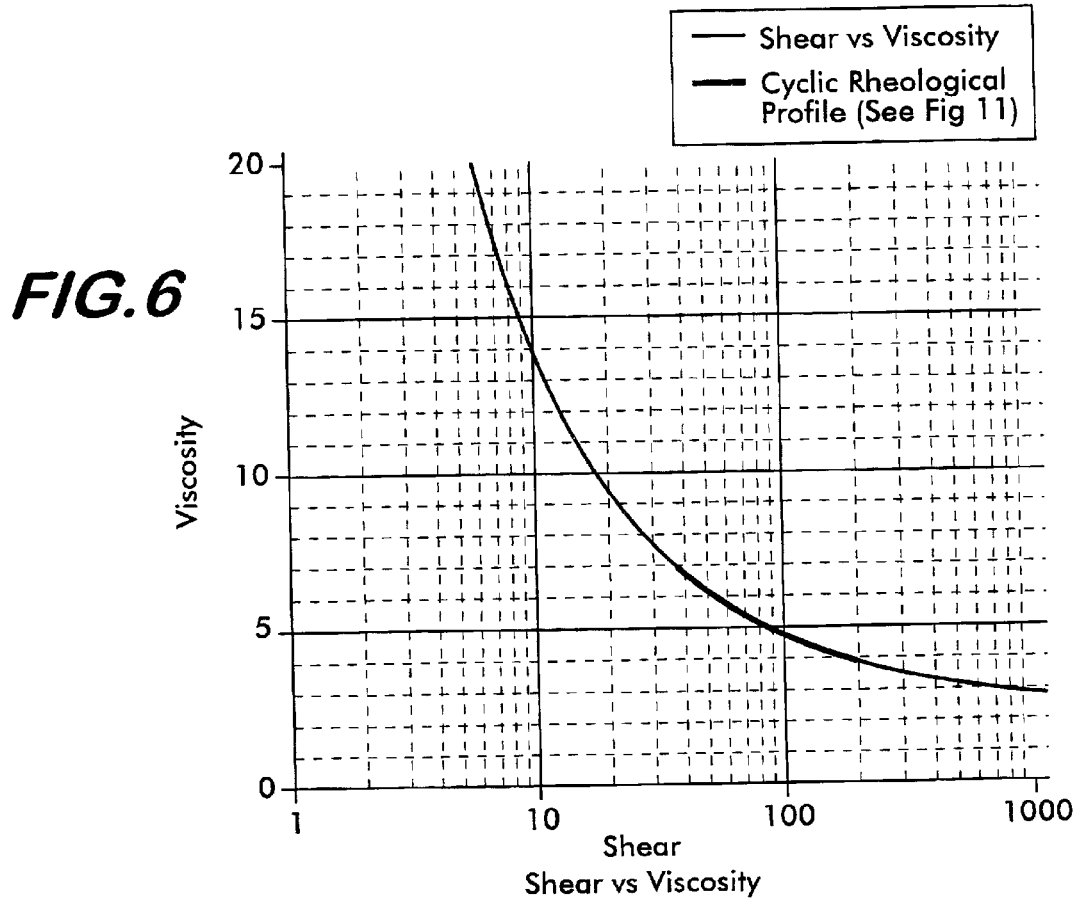
FIG. 6 is a viscosity-shear rate curve with associated cyclic rheological profile.

FIG. 6 shows the portion of the shear-viscosity curve which is actually traversed by the blood flow: the cyclic Theological profile. This is just the graph of the pair of parametric equations:

$$S = \dot{\gamma}(t).$$

$$V = \eta(t)$$

Figure 11:
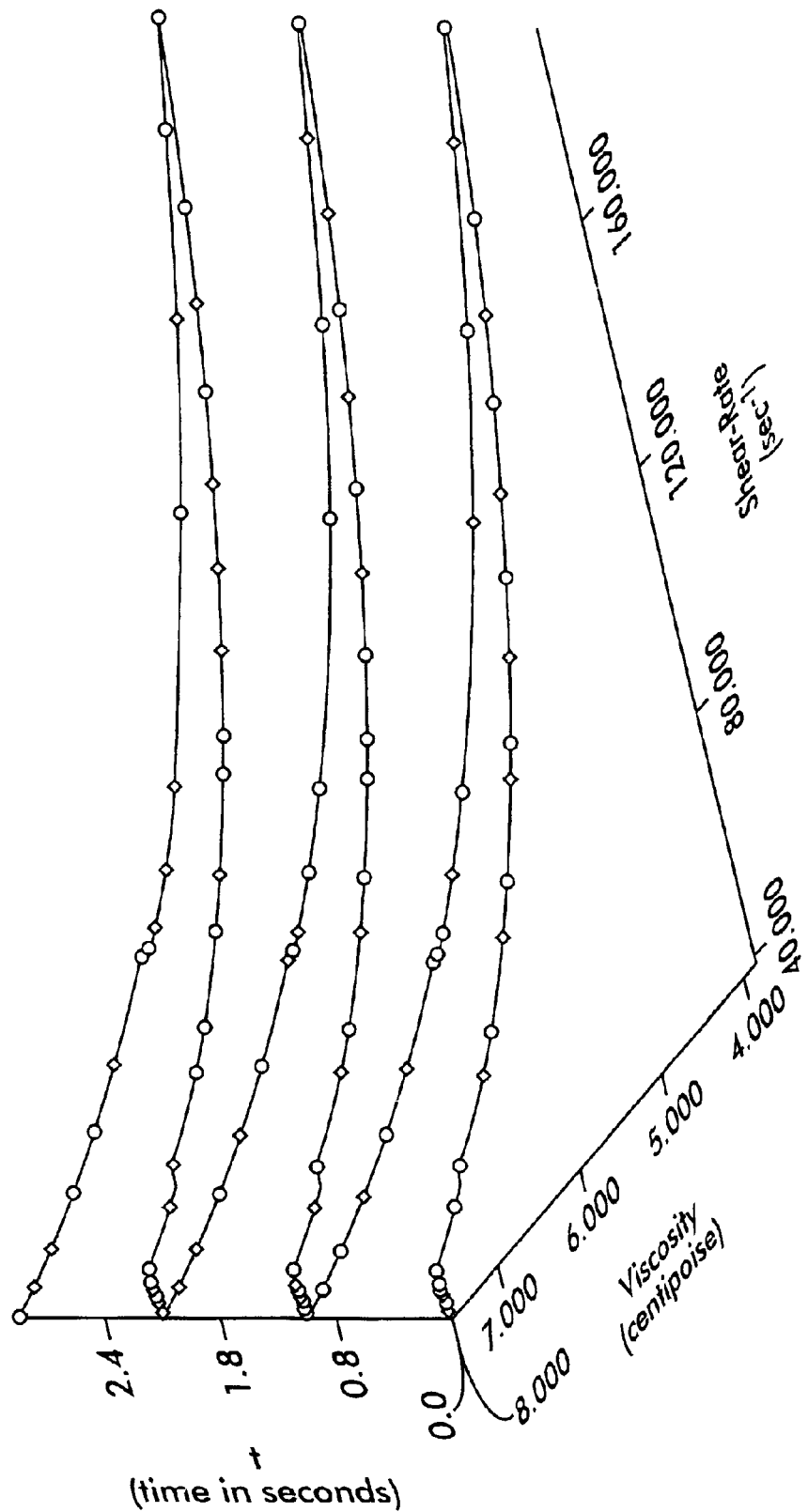
FIG. 11 is a three-dimensional plot of the viscosity, shear rate and time.

FIG. 11, shows a three-dimensional representation of the relationship between time, shear and viscosity. This graph shows not only which shear-viscosity pairs are traversed, but the time sequence of the traversal.

In this example, the average cyclic rheological profile is given by:

$$\eta_{ave} = 5.58$$

The viscosity ranges between 3.89 and 6.90. The time average of the viscosity values is 5.58.

Cyclic Rheological Profile Algorithm

The technique for calculating the functions $\dot{\gamma}(t)$ and $\eta(t)$ are referred to as the cyclic rheological profile algorithm which comprises two parts:

(1) computations using a "virtual" artery (e.g., the capillary tube 22 in the DRSC viscometer 20); and
(2) adjustment of the computations using a "virtual" artery an "actual" artery.

Computations Using a Virtual Artery

As mentioned earlier, the capillary tube 22 of the DRSC viscometer 20 may be used as the "virtual" artery and wherein $R_c$ represents the radius of the capillary tube 22 and R represents the radii of riser tubes R1/R2. Furthermore, as described in detail earlier, the DRSC viscometer 20 is used to calculate the associated curve-fitting constants $a_1, a_2, a_3$ corresponding to the flow of the blood through the viscometer 20, as well as the constants c and $c_1$ (as defined earlier with respect to equation 2-21 and 2-23).

As defined earlier, the velocity function y(t) is given in terms of the shear stress τ by the formula (2-25):

$$y(t) = \frac{ca_2}{a_3}\left[\left(\frac{c_1}{\tau}\right)^{-1} + \frac{4}{3} - \frac{1}{21}\left(\frac{c_1}{\tau}\right)^3 - \frac{16}{7}\left(\frac{c_1}{\tau}\right)^{-1/2}\right]$$

At this point, the following function is defined:

$$h = \frac{ca_2}{a_3}\left[w^{-1} + \frac{4}{3} - \frac{1}{21}w^3 - \frac{16}{7}w^{-1/2}\right]$$

and well as its inverse function:

$$w = CT(h)$$

The quantity CT(h) is defined as the Casson transform function. This function can be evaluated for any value of h using the well-known Newton-Raphson algorithm. Using the calculated values of y(t), this allows for the calculation for each time t in the cardiac cycle, the value of $w = c_1/\tau$. As a result, the value of $\tau = \tau(t)$ for each time t in the cardiac cycle can be determined.

Furthermore, the value of the shear rate $\dot{\gamma}(t)$ is obtained at time t in the cardiac cycle:

$$\dot{\gamma}(t) = \frac{1}{a_3}\left(\sqrt{\tau(t)} - \sqrt{c_1}\right)^2$$

by applying equation (2-26).

Applying the fundamental equation 1, the cyclic rheological profile is defined:

$$\eta(t) = f_1 + \frac{f_2}{\dot{\gamma}(t)} + \frac{f_3}{\sqrt{\dot{\gamma}(t)}}$$

The average cyclic viscosity can then be determined by integrating the cyclic rheological profile over a cardiac cycle:

$$\eta_{ave} = \frac{1}{T_0}\int_0^{T_0}\eta(t)dt$$

Adjustments of the Computations of the "Virtual" Artery for An "Actual" Artery

The term $\eta^a(t)$ denotes the viscosity function of an actual artery at time t. The computation of $\eta^a(t)$ must address the following issues:

a) An actual artery possibly has different geometry (radius and length) than the virtual artery.
b) The radius of an actual artery varies with time, pulsating due to the beating of the heart.
c) The flow rate y(t) through an actual artery is periodic with period equal to the length of a cardiac cycle, as opposed to the flow rate for the virtual artery, which is a decreasing function of t.
d) The function $\eta^a(t)$ is a periodic function of t, with period equal to the length of a cardiac cycle, as opposed to the function η(t), which is a decreasing function of t.

To compute the function $\eta^a(t)$, the following ingredients are necessary:

i. The curve-fitting parameters $a_1, a_2, a_3$ determined in testing the blood in the "virtual" artery.
ii. The viscosity function η(t) determined using the computations described previously.
iii. The following physical constants describing the actual artery: $y_y$=the velocity of blood in the artery at systole, $y_d$=the velocity of blood in the artery at diastole, $R_s$=the radius of the artery at systole, $R_d$=the radius of the artery at diastole
iv. The pulse-pressure function P(t) giving the pressure in the artery at time t during a cardiac cycle $0 \leq t \leq T_0$, where $T_0$ is the length of a cardiac cycle.

The manner of obtaining the ingredients i. and ii was described previously. The pulse-pressure function iv. is determined using a measuring device under development by the Assignee, namely, Rheologics, Inc. Determination of the physical constants of iii will be discussed below.

Using the ingredients i.–iv., the computation of the viscosity function $\eta^a(t)$ may be described as follows:

1. Use the pressure function P(t), the constants described below (e.g., g, ρ, $R_c$, etc.)., and the Windkessel model to determine the flow rate y(t).
2. Describe the pulsation of the artery using a model which reflects the properties required of arterial compliance in the artery. Let R(t) denote the radius of the artery as a function of time. The function R(t) is determined from the compliance model and the values of the constants iii.
3. Determine the cyclic rheological profile function $\eta^a(t)$ for an "actual" artery in terms of the "virtual" cyclic rheological profile η(t), the actual flow rate y(t) using the pressure function P(t)., and the radius R(t).
4. Determine the actual average cyclic viscosity $\eta_{ave}^a$ by integrating the cyclic rheological profile function $\eta^a(t)$.

Before proceeding to the determination of the pressure function, P(t), as mentioned earlier, the DRSC viscometer 20 comprises a U-shaped device with two identical riser tubes connected by a capillary tube 22 of significantly smaller diameter. A "falling column of fluid 82 is generated and a rising column of fluid 84 is generated. During the period before equilibrium is achieved, the heights of the fluid columns are measured at equal time intervals of length Δt=0.02 seconds. Using the algorithm described earlier, the shear rate and viscosity are estimated at the endpoints of the various time intervals. Using $\dot{\gamma}$ to denote the shear rate and η the viscosity, then both are functions of time, and form parametric equations:

$$\dot{\gamma} = \dot{\gamma}(t).$$

$$\eta = \eta(t)$$

Using the following notations:
g=gravitational acceleration in meters/$s^2$;
ρ=the density of the fluid being tests in kg/$m^3$;
$R_c$=the radius of the capillary tube in meters;
L=the length of the capillary tube in meters;
y(t)=the mean flow velocity at the riser tube in meters/second;
$R_r$=the (common) radius of the riser tubes in meters;
$x_1(t)$=the height of the falling tube in meters at time t;

$x_2(t)$=the height of the riser tube in meters at time t;
$\tau=\tau(t)$=the shear stress in the capillary wall at time t;
$\eta=\eta(t)$=the shear rate in the capillary at time t;
$\Delta h_{st}=a_1$=the additional height in the rising column of fluid due to surface tension;
$\Delta=\Delta(t)=x_1(t)-x_2(t)-a_1$;
$\tau_y$=the yield stress in the capillary tube 22.
The shear stress, shear rate and yield stress are related by the Casson model:

$$\sqrt{\tau} = \begin{cases} \sqrt{\tau_y} + \sqrt{a_3\dot{\gamma}} & \text{for } \tau \geq \tau \\ 0 \text{ and } \dot{\gamma}=0 & \text{for } 0 \leq \tau < \tau \end{cases} \quad (3\text{-}1)$$

where $a_3$ is a constant which depends only on the geometry of the DRSC viscometer 20 and not on t.
Define the constants $a_2$ and $r_1$ by the relations:

$$\tau_1 = \frac{\rho g R_c}{2L} a_2 \quad (3\text{-}2)$$

$$r_1 = \frac{R_c a_2}{\Delta}$$

results in the following formulas:

$$y(t) = \frac{c a_2}{a_3}\left[\left(\frac{c_1}{\tau}\right)^{-1} + \frac{4}{3} - \frac{1}{21}\left(\frac{c_1}{\tau}\right)^3 - \frac{16}{7}\left(\frac{c_1}{\tau}\right)^{-1/2}\right] \text{ and} \quad (3\text{-}3)$$

$$\dot{\gamma} = \frac{1}{a_3}\left(\sqrt{\tau} - \sqrt{c_1}\right)^2, \text{ where} \quad (3\text{-}4)$$

$$c = \frac{\rho g R_c}{8 R_c^2 L} \text{ and} \quad (3\text{-}5)$$

$$c_1 = \frac{\rho g R_c a_2}{2L}. \quad (3\text{-}6)$$

The fundamental relationship between shear rate and viscosity:

$$\eta = f_1 + \frac{f_2}{\dot{\gamma}} + \frac{f_3}{\sqrt{\dot{\gamma}}} \quad (3\text{-}7)$$

where the coefficients, $f_1, f_2, f_3$ are given by:

$$f_1 = a_3 \quad (3\text{-}8)$$

$$f_2 = \frac{a_2 \rho g R_c}{2L}$$

$$f_3 = \sqrt{\frac{2\rho g R_c a_2 a_3}{L}}$$

Pulse Pressure Curves

As mentioned earlier, P(t) denotes the blood pressure in an artery at time t and can be obtained using pulse pressure data collected by a pulse pressure device. For example, the device may comprise an arm pressure cuff which auto inflates to a predetermined pressure setable in software (currently approx. 170 MM Hg). It then auto-deflates through a small orifice. After about a 1 second delay (also software setable), a pressure sensor and associated circuitry starts collecting pressure data at 400 samples per second for about 5 seconds. The data is stored in a random access memory module (RAM, e.g., Compact Flash). The cuff then rapidly deflates any remaining pressure. The data is now downloaded to a computer using a serial port and Windows hyper terminal and saved to a raw file. It is then imported into Excel and converted to appropriate numbers and graphed. The power supply is a 12V DC wall power pack It is also assumed that the format of the pulse pressure data is digitized in such a way as to be compatible with the digital form of all other data in the model, i.e., P(t) is sampled at the same rate at the functions $x_2(t)$ and y(t), and is measured in compatible units to those functions. The pulse pressure function is denoted by P(t) and represents the blood pressure in an actual artery at time t. It is also assumed that t=0 is a time of diastole, so that t=0 is a local maximum of the graph of P(t). Furthermore, it is also assumed that the function P(t) is periodic, with constant period $T_0$, where $T_0$ corresponds to the length of a cardiac cycle. It is also assumed that $t=T_d$ is the time in the cardiac cycle $0 \leq t \leq T_0$ at which diastole occurs. These assumptions imply an important assumption, namely that, for a given time t, the pressure P(t) is the same throughout the artery. In fact, the pressure wave propagates through the artery at a finite speed, so that the pressure varies throughout the artery at a particular time. This fact is ignored in the analysis that follows.

The Windkessel model, which connects blood pressure with the flow rate through the artery, is selected. The Windkessel model [3, p. 163] asserts that:

$$y = C\frac{dP}{dt} + \frac{P}{R}, \quad (4\text{-}1)$$

where C and R are constants, denoting arterial compliance and peripheral resistance, respectively.

Consider the above differential equation in the interval $0 \leq t \leq T_0$, where $T_0$ denotes the length of a single cardiac cycle. Let t=0 correspond to systole and let $T_d$ denote the time of diastole within the interval. Set $$P_s = P(0) \quad (4\text{-}2)$$

$$P_d = P(T_d)$$

$$y_s = y(0)$$

$$y_d = y(T_d)$$

$$\dot{P}_s = \frac{dP}{dt}\bigg|_{t=0}$$

$$\dot{P}_d = \frac{dP}{dt}\bigg|_{t=T_d}$$

It is assumed that these last six parameters can be measured calculated. (See the discussion below.) Then the values of C and R may be determined from these parameter values as follows: Consider the differential equation (1) for t=0 and $t=T_d$ to obtain:

$$y_s = C\dot{P}_s + \frac{P_s}{R} \quad (4\text{-}3)$$

$$y_d = C\dot{P}_d + \frac{P_d}{R}$$

Set S=1/R and write the equations (3) in the form:

$$y_s = C\dot{P}_s + P_s S$$

$$y_d = C\dot{P}_d + P_d S \quad (4\text{-}4)$$

This is a system of two linear equations in two unknowns C,S. By Cramer's Rule, we have:

$$C = \frac{\begin{vmatrix} y_s & P_s \\ y_d & P_d \end{vmatrix}}{\begin{vmatrix} \dot{P}_s & P_s \\ \dot{P}_d & P_d \end{vmatrix}} \quad (4\text{-}5)$$

$$S = \frac{\begin{vmatrix} \dot{P}_s & y_s \\ \dot{P}_d & y_d \end{vmatrix}}{\begin{vmatrix} \dot{P}_s & P_s \\ \dot{P}_d & P_d \end{vmatrix}}$$

so that:

$$C = \frac{\begin{vmatrix} y_s & P_s \\ y_d & P_d \end{vmatrix}}{\begin{vmatrix} \dot{P}_s & P_s \\ \dot{P}_d & P_d \end{vmatrix}} = \frac{y_s P_d - y_d P_s}{\dot{P}_s P_d - \dot{P}_d P_s} \quad (4\text{-}6)$$

$$R = \frac{\begin{vmatrix} \dot{P}_s & P_s \\ \dot{P}_d & P_d \end{vmatrix}}{\begin{vmatrix} \dot{P}_s & y_s \\ \dot{P}_d & y_d \end{vmatrix}} = \frac{\dot{P}_s P_d - \dot{P}_d P_s}{y_d \dot{P}_s - y_s \dot{P}_d}$$

Equation (4-6) gives the values of C and R in terms of the parameters (4-2). For our purposes, the pressure function P(t) is known. The derivative $$\frac{dP}{dt}$$

can be determined by numerical differentiation from P(t). The value of $T_d$ may be determined by locating the value of t at which P(t) is minimized. The values of $P_s, P_d, \dot{P}_s, \dot{P}_d$ may then be determined.

Making the following assumption is made that the values of the two velocities $y_s$, $y_d$ are known. Then by using equation (4-6), the values of R and C may be computed. Finally, using the Windkessel equation (1), function y(t) may be computed. Therefore, the following result has been proven:

THEOREM 4.1. Assume that the velocities $y_d$, $y_s$ and the pressure function P(t) are known. Then:

1. The derivative $\dot{P}(t)$ may be calculated by differentiating P(t) numerically.
2. The value of $T_d$ may be determined as the time at which P(t) assumes its minimum value.

Using the results of 1. and 2., the values of $y_s, y_d, P_s, P_d, \dot{P}_s, \dot{P}_d$ may be computed. The velocity function y(t) may then be calculated using the formula:

$$y(t) = C\dot{P}(t) + \frac{P(t)}{R}, \quad (4\text{-}7)$$

where $$C = \frac{y_s P_d - y_d P_s}{\dot{P}_s P_d - \dot{P}_d P_s}. \quad (4\text{-}8)$$

$$R = \frac{\dot{P}_s P_d - \dot{P}_d P_s}{y_d \dot{P}_s - y_s \dot{P}_d}$$

The Casson Transform

The following describes the derivation of the Casson Transform and the supporting equations necessary for the algorithm for computing the Casson Transform. Starting with the equation for the velocity function y(t):

$$y(t) = \frac{ca_2}{a_3}\left[\left(\frac{c_1}{\tau}\right)^{-1} + \frac{4}{3} - \frac{1}{21}\left(\frac{c_1}{\tau}\right)^3 - \frac{16}{7}\left(\frac{c_1}{\tau}\right)^{-1/2}\right]$$

This suggests defining the function:

$$y = \frac{ca_2}{a_3}\left[x^{-1} + \frac{4}{3} - \frac{1}{21}x^3 - \frac{16}{7}x^{-1/2}\right] \quad (5\text{-}1)$$

where $a_2, a_3$ are parameters and c is the constant defined by:

$$c = \frac{\rho g R_c^4}{8 R_1^2 L} \quad (5\text{-}2)$$

This constant depends on the physical properties of blood and the geometry of the measuring apparatus.

Figure 12:
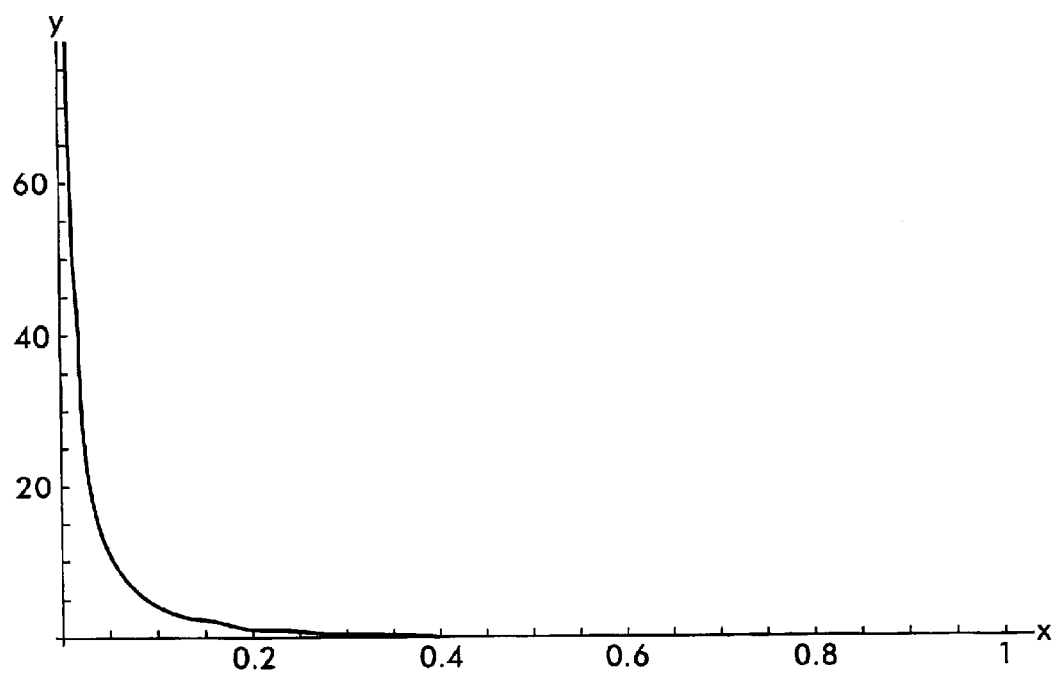
FIG. 12 depicts a graph of an equation of the form y=f(x)used in deriving a specialized transform, namely, a Casson Transform, for those values of x that result in non-negative values of y.

Using a graphing program (e.g., Mathematica) to graph the function $$x^{-1} + \frac{4}{3} - \frac{1}{21}x^3 - \frac{16}{7}x^{-1/2}$$

the graph of FIG. 12 is obtained. The graph in FIG. 12 shows that the function is monotone decreasing for $0 < x \leq 1$. A further analysis shows that the function is negative for $x > 1$. Therefore, since y(t)>0 from physical considerations, then:

$$\frac{c_1}{\tau} < 1 \Rightarrow \tau > c_1 \quad (5\text{-}3)$$

Since the function y is monotone for $0 < x \leq 1$, then y has an inverse function, which is denoted CT(y), and defined by the property:

$$x = CT(y) \Leftrightarrow y = y(x) \quad (5\text{-}4)$$

The function CT(y) is called the Casson Transform corresponding to the parameter values $a_2, a_3$. To emphasize the dependence on the parameters, the Casson Transform is sometimes denoted as $CT(y; a_2, a_3)$.

Since CT(y) is defined as an inverse function, its properties can be deduced from those of the function y=y(x), namely:

CT(y) is defined for $0 < y < \infty$.
CT(y) is monotone decreasing throughout its domain.
CT(y) is concave up throughout its domain.
CT(y) is has continuous first and second derivatives throughout its domain.
The value of the function x=CT(y) for a given value of y can be obtained as the unique solution of the equation:

$$y = \frac{ca_2}{a_3}\left[x^{-1} + \frac{4}{3} - \frac{1}{21}x^3 - \frac{16}{7}x^{-1/2}\right] \quad (5\text{-}5)$$

Since the Casson Transform is smooth and concave up, Newton's method can be applied to solve the above equation. Based on empirical observation, it is possible to define $x_0 = 0.00001$.

Moreover, again based on empirical observation, the values of $y_0$ are restricted to satisfy $0 < y_0 \leq 0.005$. (For this range of values and the above choice of initial value for x, the values of $x_k$ in the iteration, which involve square roots, are well-defined.) Then the value x corresponding to a particular value of $y_0$ can be obtained as the limit of the sequence of iterations $x_0, x_1, \ldots, x_k, x_{k+1}, \ldots$, where:

$$x_{k+1} = x_k - \frac{y(x_k) - y_0}{y'(x_k)} \quad (k = 0, 1, \ldots) \quad (5\text{-}6)$$

Since $$y'(x) = \frac{ca_2}{a_3}\left[-x^{-2} - \frac{1}{7}x^2 + \frac{8}{7}x^{-3/2}\right]$$

the iteration for obtaining x may be written in the form:

$$x_{k+1} = x_k - \frac{\frac{ca_2}{a_3}\left[x_k^{-1} + \frac{4}{3} - \frac{1}{21}x_k^3 - \frac{16}{7}x_k^{-1/2}\right] - y_0}{\frac{ca_2}{a_3}\left[-x_k^{-2} - \frac{1}{7}x_k^2 + \frac{8}{7}x_k^{-3/2}\right]} \quad (5\text{-}7)$$

$$= x_k + \frac{x_k + \frac{4}{3}x_k^2 - \frac{1}{21}x_k^5 - \frac{16}{7}x_k^{-3/2} - \frac{a_3}{ca_2}y_0 x_k^2}{1 + \frac{1}{7}x_k^4 - \frac{8}{7}x_k^{1/2}}$$

$$= x_k + \frac{21x_k + 28x_k^2 - x_k^5 - 48x_k^{3/2} - \frac{21a_3}{ca_2}y_0 x_k^2}{21 + 3x_k^4 - 24x_k^{1/2}}$$

$$= \frac{42x_k + 28x_k^2 + 2x_k^5 - 72x_k^{3/2} - \frac{21a_3}{ca_2}y_0 x_k^2}{21 + 3x_k^4 - 24x_k^{1/2}} \quad (k = 0, 1, \ldots)$$

This last equation results in the following:

THEOREM 5.1. The value of the Casson Transform x=CT(y) may be computed as the limit of the sequence $x_0, x_1, x_2, \ldots$, where $x_0 = 0.001$ and $$x_{k+1} = \frac{42x_k + 28x_k^2 + 2x_k^5 - 72x_k^{\frac{3}{2}} - \frac{21a_3}{ca_2}yx_k^2}{21 + 3x_k^4 - 24x_k^{\frac{1}{2}}}, \quad (5\text{-}8)$$

Moreover, as discussed previously, if $\tau$ denotes the shear stress at time t, then the velocity $y=y(t)$ and $\tau$ are related by the equation:

$$y(t) = \frac{ca_2}{a_3}\left[\left(\frac{c_1}{\tau}\right)^{-1} + \frac{4}{3} - \frac{1}{21}\left(\frac{c_1}{\tau}\right)^3 - \frac{16}{7}\left(\frac{c_1}{\tau}\right)^{-\frac{1}{2}}\right]$$

where $$c_1 = \frac{\rho g R_t}{2L} a_2 \quad (5\text{-}9)$$

Therefore:

$$\frac{c_1}{\tau} = CT(y)$$

or equivalently $$\tau = \frac{\rho g R_c}{2L} \frac{a_2}{CT(y)}$$

Furthermore, this also results in the following:

THEOREM 5.2. The velocity $y=y(t)$ and the shear stress $\tau=\tau(t)$ are related by the equation:

$$\tau = \frac{\rho g R_c}{2L} \frac{a_2}{CT(y)} \quad (5\text{-}10)$$

where CT(y) denotes the Casson Transform, whose value may be calculated using Theorem 5.1.

As mentioned earlier, from the value of the shear stress $\tau$, the shear rate may be obtained from the standard formula:

$$\dot{\gamma}(t) = \frac{1}{a_3}\left(\sqrt{\tau(t)} - \sqrt{c_1}\right)^2 \quad (5\text{-}11)$$

where the constant $c_1$ is given in equation (5-9) above. Inserting the values of $\tau$ from equation (5-10) and $c_1$ from (5-9), the following result is:

$$\dot{\gamma} = \frac{1}{a_3}\left[\sqrt{\frac{\rho g R_t}{2L}\frac{a_2}{CT(y)}} - \sqrt{\frac{\rho g R_t}{2L}a_2}\right]^2 \quad (5\text{-}12)$$

$$= \frac{\rho g R_t}{2L}\frac{a_2}{a_3}\left[\frac{1}{\sqrt{CT(y)}} - 1\right]^2$$

This formula is of interest since it expresses the shear rate directly in terms of the velocity y. THEOREM 5.3. The shear rate $\dot{\gamma}$ is given in terms of the velocity y by the formula:

$$\dot{\gamma} = \frac{\rho g R_c}{2L}\frac{a_2}{a_3}\left[\frac{1}{\sqrt{CT(y)}} - 1\right]^2. \quad (5\text{-}13)$$

Applying the fundamental relationship between shear rate and viscosity:

$$\eta = f_1 + \frac{f_2}{\dot{\gamma}} + \frac{f_3}{\sqrt{\dot{\gamma}}} \quad (5\text{-}14)$$

where $$f_1 = a_3 \quad (5\text{-}15)$$

$$f_2 = \frac{a_2 \rho g R_t}{2L}$$

$$f_3 = \sqrt{\frac{2\rho g R_t a_2 a_3}{L}}$$

Applying equations (5-15) and (5-13) to equation (5-14), the result is:

$$\eta = f_1 + \frac{f_2}{\frac{\rho g R_c}{2L}\frac{a_2}{a_3}\left[\frac{1}{\sqrt{CT(y)}} - 1\right]^2} + \frac{f_3}{\sqrt{\frac{\rho g R_c}{2L}\frac{a_2}{a_3}\left[\frac{1}{\sqrt{CT(y)}} - 1\right]}}$$

$$= a_3 + \frac{\frac{a_2 \rho g R_c}{2L}}{\frac{\rho g R_c}{2L}\frac{a_2}{a_3}\left[\frac{1}{\sqrt{CT(y)}} - 1\right]^2} + \frac{\sqrt{\frac{2\rho g R_c a_2 a_3}{L}}}{\sqrt{\frac{\rho g R_c}{2L}\frac{a_2}{a_3}\left[\frac{1}{\sqrt{CT(y)}} - 1\right]}}$$

$$= a_3 + \frac{a_3}{\left[\frac{1}{\sqrt{CT(y)}} - 1\right]^2} + \frac{2a_3}{\left[\frac{1}{\sqrt{CT(y)}} - 1\right]}$$

-continued $$= a_3\left(1 + \frac{1}{\left[\frac{1}{\sqrt{CT(y)}} - 1\right]^2} + \frac{2}{\left[\frac{1}{\sqrt{CT(y)}} - 1\right]}\right)$$

This proves the following formula which expresses viscosity in terms of the velocity y.

THEOREM 5.4. At velocity y, the viscosity is given by the formula:

$$\eta = a_3\left(1 + \frac{2}{\Lambda(y)} + \frac{1}{\Lambda(y)^2}\right) \tag{5-16}$$

where $$\Lambda(y) = \frac{1}{\sqrt{CT(y)}} - 1 \tag{5-17}$$

Dependence on Capillary Geometry

The following discussion concerns what happens when the radius of the capillary tube 22 varies but that the radii of the riser tubes R1/R2 containing the rising and falling columns of fluid are kept the same. In particular, it is important to assess the impact on all formulas in the model and the values of the curve-fitting parameters $a_1, a_2, a_3$. Denote the new situation (varied capillary tube radius and/or length) using * on all previously-defined variables. Assume that:

$R_c^* = kR_c$ $R^* = R \tag{6-1}$

Since the radius of the riser tube is unchanged, the additional height caused by surface tension is the same in both systems:

$a_1^* = a_1 \tag{6-2}$

In the Casson model, the quantities yield stress $\tau_s$ and the model constant $a_3$ depend only on the fluid sample and not on the geometry of the flow. And therefore:

$$\tau_l = \frac{\rho g R_c'}{2L} a_2' = \frac{\rho g R_c}{2L} a_2 \tag{6-3}$$

$$\frac{\rho g \cdot k R_c}{2L} a_2^* = \frac{\rho g R_c}{2L} a_2$$

$$a_2^* = \frac{1}{k} a_2$$

$$a_3^* = a_3$$

In similar fashion, if $L' = jL$, then $a_1^* = a_1$ $a_2^* = j a_2$ $a_3^* = a_3 \tag{6-4}$ Which results in the following:

THEOREM 6.1. If the radius and length of the capillary tube 22 are changed, respectively, by factors of k and j, so that:

$R_c^* = kR_c$ $L^* = jL \tag{6-5}$ then the curve-fitting parameters change as follows:

$a_1^* = a_1 \tag{6-6}$ $a_2^* = \frac{j}{k} a_2$ $a_3^* = a_3$

Utilizing Theorem 6.1 to determine how the remainder of the constants and functions of the equations 5- transform when the radius and length of the capillary tube 22 change from $R_c, L$ to $R_c^*, L^*$, respectively. Starting with the constants c and $c_1$:

$$c = \frac{\rho g R_c^4}{8 R_r^2 L} \tag{6-7}$$

$$c_1 = \frac{\rho g R_c}{2L} a_2 \text{ so that}$$

$$c^* = \frac{\rho g R_c^{*4}}{8 R_r^2 L^*} \tag{6-8}$$

$$c_1^* = \frac{\rho g R_c^*}{2L^*} a_2^*$$

so that by equation (6-1) and Theorem 6.1, and therefore:

$$c^* = \frac{k^4 \rho g R_c^4}{8 R_i^2 jL} \tag{6-9}$$

$$= \frac{k^4}{j} c$$

$$c_1^* = \frac{\rho g R_c^*}{2L^*} a_2^* \tag{6-10}$$

$$= \frac{k \rho g R_c^*}{2jL} \frac{j}{k} a_2$$

$$= c_1$$

Next consider the transform property of the function:

$$y(x) = \frac{c a_2}{a_3}\left[x^{-1} + \frac{4}{3} - \frac{1}{21}x^3 - \frac{16}{7}x^{-\frac{1}{2}}\right].$$

where:

$$y^*(x) = \frac{c^* a_2^*}{a_3^*}\left[x^{-1} + \frac{4}{3} - \frac{1}{21}x^3 - \frac{16}{7}x^{-1/2}\right] \tag{6-11}$$

$$= \frac{k^4}{j} \cdot \frac{j}{k} \frac{c a_2}{a_3}\left[x^{-1} + \frac{4}{3} - \frac{1}{21}x^3 - \frac{16}{7}x^{-1/2}\right]$$

$$= k^3 \frac{c a_2}{a_3}\left[x^{-1} + \frac{4}{3} - \frac{1}{21}x^3 - \frac{16}{7}x^{-1/2}\right]$$

$$= k^3 y(x)$$

To determine the inverse function $CT^*(y^*)$, it should be noted that the solution $x^*$ of the equation $$y^* = \frac{c^* a_2^*}{a_3^*}\left[x^{*-1} + \frac{4}{3} - \frac{1}{21}x^{*3} - \frac{16}{7}x^{*-1/2}\right] \tag{6-12}$$

is the same as the equation $$k^{-3} y^*(x^*) = \frac{ca_2}{a_3}\left[x^{*-1} + \frac{4}{3} - \frac{1}{21}x^{*3} - \frac{16}{7}x^{*-1/2}\right] \quad (6\text{-}13)$$

by (6-11), so that:

$$x^* = CT(k^{-3} y^*) \quad (6\text{-}14)$$

That is:

$$CT^*(y^*) = CT(k^{-3} y^*) \quad (6\text{-}15)$$

Applying equation (6-10) to obtain:

$$\tau^* = \frac{\rho g R_c^*}{2L^*} \cdot \frac{a_2^*}{CT^*(y^*)} \quad (6\text{-}16)$$

$$= \frac{k\rho g R_c}{2lL} \cdot \frac{\frac{l}{k}a_2}{CT(k^{-3} y^*)}$$

$$= \frac{\rho g R_c}{2L} \cdot \frac{a_2}{CT(k^{-3} y^*)}$$

Similarly:

$$\dot{\gamma}^* = \frac{\rho g R_c^*}{2L^*} \cdot \frac{a_2^*}{a_3^*}\left[\frac{1}{\sqrt{CT^*(y^*)}} - 1\right]^2 \quad (6\text{-}17)$$

$$= \frac{k\rho g R_c}{2lL} \cdot \frac{l}{k} \cdot \frac{a_2}{a_3}\left[\frac{1}{\sqrt{CT(k^{-3} y^*)}} - 1\right]^2$$

$$= \frac{\rho g R_c}{2L} \cdot \frac{a_2}{a_3}\left[\frac{1}{\sqrt{CT(k^{-3} y^*)}} - 1\right]^2$$

And:

$$\Lambda^*(y)^* = \frac{1}{\sqrt{CT^*(y^*)}} - 1 \quad (6\text{-}18)$$

$$= \frac{1}{\sqrt{CT(k^{-3} y^*)}} - 1$$

$$\Lambda(k^{-3} y^*)$$

And, finally:

$$\eta^* = a_3^*\left(1 + \frac{2}{\Lambda^*(y^*)} + \frac{1}{\Lambda^*(y^*)^2}\right) \quad (6\text{-}19)$$

$$= a_3\left(1 + \frac{2}{\Lambda(k^{-3} y^*)} + \frac{1}{\Lambda(k^{-3} y^*)^2}\right)$$

Collecting the various equations of this section into the following result:

THEOREM 6.2. Let $a_1, a_2, a_3$ be the curve-fitting parameters obtained from testing a sample using a capillary of radius $R_c$. Suppose that $y = y(t)$ denotes the velocity profile in an artery of radius $R_a$ and length $L_a$. Let k and l denote the ratios defined by:

$$k = \frac{R_0}{R_c}, \; l = \frac{L_a}{L}. \quad (6\text{-}20)$$

Then the shear rate $\dot{\gamma}(t)$ and the viscosity $\eta(t)$ at time t in the artery are given by the formulas:

$$\dot{\gamma} = \frac{\rho g R_c}{2L} \cdot \frac{a_2}{a_3}\left[\frac{1}{\sqrt{CT(k^{-3} y)}} - 1\right]^2 \quad (6\text{-}21)$$

and $$\eta = a_3\left(1 + \frac{2}{\Lambda(k^{-3} y)} + \frac{1}{\Lambda(k^{-3} y)^2}\right) \quad (6\text{-}22)$$

where $$\Lambda(y) = \frac{1}{\sqrt{CT(y)}} - 1 \quad (6\text{-}23)$$

and $CT(y)$ denotes the Casson transform.

Calculation of the Cyclic Rheologic Profile—Non-pulsating Case

The pulse-pressure function P(t) for the flow through the artery at times t in the interval $0 \le t \le T_0$, where $T_0$ is the length of a single cardiac cycle is assumed to be known. Also, from the function P(t), it was previously shown how to compute the function y(t) which gives the velocity of flow through the artery. In the following discussion, it is assumed that the radius of the artery remains fixed throughout the cardiac cycle. That is, the pulsation of the artery is ignored as a function of time. This will be addressed later.

THEOREM 7.1. It is assumed that the values of the velocities $y_s = y(0)$ and $y_d = y(T_d)$ are known. Then the viscosity $\eta(t)$ at time t in a cardiac cycle is given by the formula:

$$\eta(t) = a_3\left(1 + \frac{2}{\Lambda(k^{-3} y(t))} + \frac{1}{\Lambda(k^{-3} y(t))^2}\right)(0 \le t \le T_0) \quad (7\text{-}1)$$

where:

$$\Lambda(y) = \frac{1}{\sqrt{CT(y)}} - 1 \quad (7\text{-}2)$$

and where $$k = \frac{R_a}{R_c} \quad (7\text{-}3)$$

and where the velocity function y(t) is computed using Theorem 4.1.

Calculation of the Average Cyclic Viscosity—Non-pulsating Actual Artery

To obtain the average cyclic viscosity, the value of $\eta(t)$ is averaged over a cardiac cycle:

$$\eta_{ave} = \frac{1}{T_0}\int_0^{T_0} \eta(t)dt.$$

And by equation (7-1), the average cyclic viscosity may be computed as:

$$\eta_{ave} = \frac{a_3}{T_0}\int_0^{T_0}\left(1 + \frac{2}{\Lambda(k^{-3} y(t))} + \frac{1}{\Lambda(k^{-3} y(t))^2}\right)dt \quad (8\text{-}1)$$

$$= \frac{a_3}{T_0}\left(\int_0^{T_0} dt + 2\int_0^{T_0} \frac{dt}{\Lambda(k^{-3} y(t))} + \int_0^{T_0} \frac{dt}{\Lambda(k^{-3} y(t))^2}\right)$$

-continued $$= a_3 + \frac{2a_3}{T_0} \int_0^{T_0} \frac{dt}{\Lambda(k^{-3}y(t))} + \frac{a_3}{T_0} \int_0^{T_0} \frac{dt}{\Lambda(k^{-3}y(t))^2}$$

This proves the following result:

THEOREM 8.1. The average cyclic viscosity $\eta_{ave}$ is given by the formula:

$$\eta_{ave} = a_3 + \frac{2a_3}{T_0} \int_0^{T_0} \frac{dt}{\Lambda(k^{-3}y(t))} + \frac{a_3}{T_0} \int_0^{T_0} \frac{dt}{\Lambda(k^{-3}y(t))^2} \quad (8\text{-}2)$$

where $$\Lambda(y) = \frac{1}{\sqrt{CT(y)}} - 1 \quad (8\text{-}3)$$

and where y(t) is computed using Theorem 4.1.

$$y(t) = y_0 + \frac{l}{\rho L} \int_0^t P(u)du \quad (0 \le t \le T_0) \quad (8\text{-}4)$$

In the above result, the functions of (8-3) and (8-4) are computed numerically for values of t at discrete intervals so that the integrals of (8-2) may be calculated by numerical integration.

Artery Pulsation Model

The computations thus far have assumed that the radius of the capillary tube 22 is constant with respect to time. Of course, this is not so. It is known that the radius of the artery varies in response to the changing pressure. This is due to the fact that an artery is not a rigid pipe, but rather is elastic. It can be shown that, in the case of varying pressure in an elastic pipe, increased pressure will cause the radius to increase. Let the relationship between the radius R and the pressure P be given by the function:

$$R = f(P)$$

The function $f$ depends on the elastic properties of the artery wall, varies from patient to patient, and even varies with time for a particular patient (due to exercise, stress, and arterial disease). Consider the properties that the function $f$ must satisfy. Let V denote the value of the artery when its radius is R. Then $$V = \pi R^2 L = \pi f(P)^2 L \quad (9\text{-}1)$$

where L denotes the length of the artery and where it is assumed that the artery is perfectly cylindrical. The rate of change of volume with respect to pressure is given by the derivative:

$$\frac{dV}{dP} = C$$

is called the "compliance" of the artery. The compliance is a function of the pressure in the artery: C=C(P). For a given patient and artery, the compliance function may vary with time (say due to arterial disease). However, for purposes of this analysis, it is assumed that an unchanging compliance function is present.

Since the volume of the artery increases with the pressure, the compliance is always positive. It is known (see "Cardiovascular Physiology Web Resource" by Klabunde) that the compliance function is increasing—that is, the compliance C increases with increasing pressure. Moreover, the compliance function increases at a decreasing rate, so that the graph of C with respect to P is concave down. In mathematical terms, these geometric requirements may be stated as:

$$C > 0, \frac{dC}{dP} > 0, \frac{d^2C}{dP^2} < 0. \quad (9\text{-}2)$$

The requirements (9-2) have implications for the radius-pressure relationship $f$. Namely, from equation (9-1), we have:

$$C(P) = \frac{dV}{dP} \quad (9\text{-}3)$$

$$= \frac{d}{dP}[\pi f(P)^2 L]$$

$$= 2\pi L \frac{df}{dP}$$

Since C(P)>0 implies that $$\frac{df}{dP} > 0 \quad (9\text{-}4)$$

so that $f$ is an increasing function of P. Furthermore, from (9-3), it can be seen that $$\frac{dC}{dP} = 2\pi L \frac{d^2 f}{dP^2} \quad (9\text{-}5)$$

so that the second inequality of (9-2) implies that $$\frac{d^2 f}{dP^2} > 0. \quad (9\text{-}6)$$

Finally, since $$\frac{d^2 C}{dP^2} = 2\pi L \frac{d^3 f}{dP^3} \quad (9\text{-}7)$$

the third inequality of (9-2) implies that:

$$\frac{d^3 f}{dP^3} < 0 \quad (9\text{-}8)$$

The inequalities (9-4), (9-6), and (9-8) give requirements that any radius-pressure model must satisfy.

Assuming a radius-pressure model of the form:

$$f(P) = \alpha_1(1 + \alpha_2 P^\beta) \quad (9\text{-}9)$$

where $\alpha_1, \alpha_2, \beta$ are positive constants. Since $$\frac{df}{dP} = \beta \alpha_2 P^{\beta-1} \quad (9\text{-}10)$$

$$\frac{d^2 f}{dP^2} = \beta(\beta-1)\alpha_2 P^{\beta-2}$$

-continued $$\frac{d^3 f}{dP^3} = \beta(\beta-1)(\beta-2)\alpha_2 P^{\beta-3}$$

inequality (9-4) is automatically satisfied. Furthermore, for inequality (9-6) to be satisfied, there must be:

$$\beta > 1 \qquad (9\text{-}11)$$

Finally, for inequality (9-8) to be satisfied, there must be (assuming that (9-11) is satisfied):

$$\beta < 2 \qquad (9\text{-}12)$$

In other words, the following result has been proven:
THEOREM 9.1: In order for the radius-pressure model $$f(P) = \alpha_1 (1 + \alpha_2 P^\beta)$$

to satisfy the compliance conditions (9-2), it is necessary and sufficient that $1 < \beta < 2$. Throughout the remainder of this section, a radius-pressure model of the form (9-9) is assumed, where $1 < \beta < 2$. Suppose that $P = P(t)$, where $0 \leq t \leq T_0$ corresponds to a single cardiac cycle with $t=0$ the systole and $t=T_d$ the time of diastole. Furthermore, let $R(t)$ denote the radius of the artery at time t. Then the following model for the pulsation of the artery is given:

$$R(t) = f(P(t)) = \alpha_1 (1 + \alpha_2 P(t)^\beta) \qquad (9\text{-}13)$$

The function $R(t)$ is periodic with period $T_0$. Moreover, over the single period $0 \leq t \leq T_0$, $R(t)$ assumes its maximum at $t=0$ and its minimum at $t=T_d$. Let the radius at these times be denoted by $R_s$ and $R_d$. Define the ratio $$\theta = \frac{R_d}{R_t} \qquad (9\text{-}14)$$

as the compliance constant. Since $R_d$ denotes the minimum value of $R(t)$ and $R_s$ its maximum value, the compliance constant satisfies:

$$0 < \theta < 1 \qquad (9\text{-}15)$$

This constant is a measure of how much the artery pulsates during a cardiac cycle. Let $P_s$ be the pressure at systole and $P_d$ the pressure at diastole. That is:

$$P_s = R(0)$$

$$P_d = R(T_d) \qquad (9\text{-}16)$$

Analogous to the definition of the compliance constant, set:

$$\omega = \frac{P_d}{P_s} \qquad (9\text{-}17)$$

The values of the constants $\alpha_1$ and $\alpha_2$ may be computed in terms of the $\theta$ and $\omega$ as follows: Substituting $t=0$ into equation (9-13), it can be seen that:

$$R(0) = \alpha_1 (1 + \alpha_2 P(0)^\beta)$$

$$R_s = \alpha_1 (1 + \alpha_2 P_s^\beta) \qquad (9\text{-}18)$$

Similarly, substituting $t=T_d$ into equation (9-13) gives:

$$R(T_d) = \alpha_1 (1 + \alpha_2 P(T_d)^\beta)$$

$$R_d = \alpha_1 (1 + \alpha_2 P_d^\beta) \qquad (9\text{-}19)$$

Dividing equation (9-19) by equation (9-18) gives:

$$\theta = \frac{R_d}{R_s} = \frac{1 + \alpha_2 P_d^\beta}{1 + \alpha_2 P_s^\beta} \qquad (9\text{-}20)$$

$$\theta + \theta \alpha_2 P_s^\beta = 1 + \alpha_2 P_d^\beta$$

$$\alpha_2 = -\frac{1-\theta}{P_d^\beta - \theta P_s^\beta}$$

$$= -P_s^{-\beta} \frac{1-\theta}{\left(\frac{P_d}{P_s}\right)^\beta - \theta}$$

$$= -P_s^{-\beta} \frac{1-\theta}{\omega^\beta - \theta}$$

Substituting the value of $\alpha_2$ from equation (9-20) into equation (9-19) and solving for $\alpha_1$ yields:

$$R_d = \alpha_1 (1 + \alpha_2 P_d^\beta) \qquad (9\text{-}21)$$

$$= \alpha_1 \left(1 - \frac{1-\theta}{P_d^\beta - \theta P_s^\beta} P_d^\beta\right)$$

$$= \frac{\alpha_1}{P_d^\beta - \theta P_s^\beta} (-\theta P_s^\beta + \theta P_d^\beta)$$

$$= \alpha_1 \theta \frac{P_d^\beta - P_s^\beta}{P_d^\beta - \theta P_s^\beta}$$

$$\alpha_1 = \frac{R_d}{\theta} \cdot \frac{P_d^\beta - \theta P_s^\beta}{P_d^\beta - P_s^\beta}$$

$$= \frac{R_d}{\theta} \cdot \frac{\left(\frac{P_d}{P_s}\right)^\beta - \theta}{\left(\frac{P_d}{P_s}\right)^\beta - 1}$$

$$= \frac{R_d}{\theta} \cdot \frac{\omega^\beta - \theta}{\omega^\beta - 1}$$

Re-arranging equation (9-13): Insert the values of $\alpha_1$ and $\alpha_2$ from (9-19) and (9-20), respectively, into equation (9-13) to obtain:
THEOREM 9.2: Assume that $1 < \beta < 2$, then the pulsation model is:

$$R(t) = \alpha_3 \left[1 - \alpha_4 \left(\frac{P(t)}{P_s}\right)^\beta\right] \qquad (9\text{-}22)$$

where $$\alpha_3 = \frac{R_d}{\theta} \cdot \frac{\omega^\beta - \theta}{\omega^\beta - 1} \qquad (9\text{-}23)$$

$$\alpha_4 = \frac{1-\theta}{\omega^\beta - \theta}.$$

Calculation of the Cyclic Rheological Profile-pulsating Actual Artery

The results of the preceding discussion can now be applied to obtain the cyclic rheological profile, taking into account the pulsation of the artery. Because the computation consists of many parts, the complete computation is summarized below:

1. Use the pressure function P(t) and the values of $y_s$ and $y_d$ to compute the velocity profile y(t) in the artery using Theorem 4.1.

2. Compute the curve-fitting parameters $a_1, a_2, a_3$ by testing a sample using a capillary tube 22 of radius $R_c$.

3. Next, consider a time $t$ for which $0 \leq t \leq T_0$. At this time, assume that the radius of the artery is $R=R(t)$, given by the model:

$$R(t) = \alpha_3 \left[1 - \alpha_4 \left(\frac{P(t)}{P_s}\right)^\beta\right] \quad (10\text{-}1)$$

where:

$$\alpha_3 = \frac{R_d}{\theta} \cdot \frac{\omega^\beta - \theta}{\omega^\beta - 1} \quad (10\text{-}2)$$

$$\alpha_4 = \frac{1-\theta}{\omega^\beta - \theta},$$

$\beta$ is a model parameter, and $\theta$ and $\omega$ are given by:

$$\theta = \frac{R_d}{R_s} \quad (10\text{-}3)$$

$$\omega = \frac{P_d}{P_s}$$

and $R_d$, $R_s$ denote the radius at diastole and systole, respectively, and $P_d$, $P_s$ denote, respectively, the pressure at diastole and systole, respectively.

4. Next, let $k$ and $l$ denote the ratios defined by:

$$k = \frac{R(t)}{R_c}, \quad l = \frac{L_a}{L}. \quad (10\text{-}4)$$

Then the shear rate $\dot{\gamma}^a(t)$ and the viscosity $\eta^a(t)$ at time $t$ in the artery are given by the formulas:

$$\dot{\gamma}^a = \frac{\rho g R_c}{2L} \cdot \frac{a_2}{a_3} \left[\frac{1}{\sqrt{CT(k^{-3}y)}} - 1\right]^2 \text{ and} \quad (10\text{-}5)$$

$$\eta^a = a_3 \left(1 + \frac{2}{\Lambda(k^{-3}y)} + \frac{1}{\Lambda(k^{-3}y)^2}\right) \quad (10\text{-}6)$$

where $$\Lambda(y) = \frac{1}{\sqrt{CT(y)}} - 1 \quad (10\text{-}7)$$

and $CT(y)$ denotes the Casson transform.

Calculation of the Average Cyclic Viscosity-pulsating Actual Artery

As mentioned earlier, the average cyclic viscosity $\eta_{ave}$ can be computed in the pulsating case using the formula:

$$\eta^a_{ave} = a_3 + \frac{2a_3}{T_0} \int_0^{T_0} \frac{dt}{\Lambda(k^{-3}y(t))} + \frac{a_3}{T_0} \int_0^{T_0} \frac{dt}{\Lambda(k^{-3}y(t))^2} \quad (11\text{-}1)$$

where, in the pulsating case, the value of $k$ is given as:

$$k = \frac{R(t)}{R_c} \quad (11\text{-}2)$$

and $$\Lambda(y) = \frac{1}{\sqrt{CT(y)}} - 1 \quad (11\text{-}3)$$

and $y(t)$ is calculated from $P(t)$ using Theorem 4.1.

Calculating Physical Constant Values

The various computations discussed in this application require physical constants. The computations described in this application assume that the following constants are known:

$$y_s, y_d, R_s, R_d, \beta$$

The only restriction placed on $\beta$ is that it lie in the interval $1 < \beta < 2$. Some experimentation is required to determine a value of $\beta$ in this interval which gives the most accurate pulsation model for a particular artery being considered. Prior to such experimentation, the computations set $$\beta = \frac{3}{2}.$$

At the time of systole, the value of pressure is a maximum as is the radius. Thus, $R_s$ represents the maximum artery radius. For initial computations, an average value is assumed for a particular artery, independent of the particular subject used. For more accurate computations, the value of $R_s$ may be determined using an MRI. Similarly, $R_d$ represents the minimum value of the artery radius. Based on experiment, it is possible to determine an approximation for the ratio $R_d/R_s$ and use this experimental ratio, independent of the subject. In the absence of such experimental values, it is assumed that this ratio is 0.5. That is, it is assumed that the artery contracts to half its radius from systole to diastole. Assuming that the ratio $R_d/R_s$ is known, then the value of $R_d$ may be determined from the value of $R_s$. For a more accurate approach, the value of $R_d$ may be determined using an MRI.

The approach to determining the velocity values $y_s$ and $y_d$ can mimic the approach to determining $R_s$ and $R_d$. Namely, average values can be assumed for a particular artery for a simple, subject-independent approach or a more elaborate approach can be used to obtain subject-dependent values. In all cases, using a subject-independent approach may be used for general screening, and a subject-dependent approach where arterial disease is present or suspected.

While the invention has been described in detail and with reference to specific examples thereof, it will be apparent to one skilled in the art that various changes and modifications can be made therein without departing from the spirit and scope thereof.

What is claimed is:

1. A method for determining the viscosity of blood flowing through the cardiovascular system of a living being at any point in the system, said method comprising the steps of:

(a) determining a characteristic relationship for the blood between viscosity and shear rate, said step of determining a characteristic relationship comprising:

(1) subjecting a portion of the blood to a plurality of shear rates as the blood flows through a device, said device comprising a scanning viscometer having a capillary tube and at least one riser tube, said device having some known parameters including the diameter and length of said capillary tube and the diameter of said at least one riser tube;

(2) collecting a plurality of data points corresponding to movement of the blood through said plurality of shear rates, said collected data points corresponding to the changing height of at least one column of blood that moves through said capillary tube and said at least one riser tube, said at least one column of blood comprising a rising column of blood and a falling column of blood; and (3) using said collected data points and some known parameters of said device to generate said characteristic relationship, said characteristic relationship comprising an equation that describes the viscosity of the blood in terms of the shear rate of the blood, said shear rates of the blood being variable from approximately zero shear rate to infinite shear rate, said use of said collected data points comprising:

(i) computing estimated values of the mean flow velocity of the blood as it flows through said device;

(ii) selecting a first model for a constitutive equation that relates shear rate with shear stress, said first model comprising a Casson model based on:

$$\sqrt{\tau} = \begin{cases} \sqrt{\tau_y} + \sqrt{a_3 \dot{\gamma}} & \text{for } \tau \geq \tau_y \\ 0 \text{ and } \dot{\gamma} = 0 & \text{for } 0 \leq \tau < \tau_y \end{cases}$$

where $\tau$ represents the shear stress of the blood;

$\tau_r$ represents the yield stress of the blood and is constant;

$\dot{\gamma}$ is the shear rate of the blood; and $a_3$ is a constant and is one of said constitutive equation parameters that minimizes the sum of squares of the deviations of said theoretical values of said mean flow velocity and said estimated values of said mean flow velocity;

(iii) applying said constitutive equation and principles of fluid dynamics to determine a second model that provides the mean flow velocity of the blood as a function of time along with physical and constitutive equation parameters and which generates theoretical values of the mean flow velocity;

(iv) substituting said collected data points into said second model to generate an over-determined system of equations for said constitutive equation parameters;

(v) applying a non-linear curve-fitting algorithm to determine the values of said constitutive equation parameters that minimize the sum of squares of the deviations of said theoretical values of the mean flow velocity and said estimated values of said mean flow velocity; and (vi) using said determined values of said constitutive equation parameters to generate said characteristic relationship for the blood between viscosity and shear rate, and wherein said characteristic relationship comprises a characteristic blood viscosity-shear rate relationship as follows:

$$V = f_1 + \frac{f_2}{S} + \frac{f_3}{\sqrt{S}}$$

where

V is said viscosity of the blood;

S is the shear rate of the blood; and $f_1$, $f_2$ and $f_3$ are constant coefficients that are defined as:

$f_1 = a_3$ $$f_2 = \frac{a_2 \rho g R_c}{2L}$$

$$f_3 = \sqrt{\frac{2\rho g R_c a_2 a_3}{L}}$$

where $R_c$ is the radius of said capillary tube

L is the length of said capillary tube;

$\rho$ is the density of the blood;

g is the gravitational constant; and $a_2$ is another one of said constitutive equation parameters that minimizes the sum of squares of the deviations of said theoretical values of said mean flow velocity and said estimated values of said mean flow velocity; and (b) obtaining a shear rate of the blood as it moves through at least one position in the system; and (c) determining the viscosity of the blood at said at least one position by applying said shear rate to said characteristic relationship.

2. The method of claim 1 wherein said step of determining the shear stress of the blood at said at least one position by multiplying said determined viscosity of the blood at said at least one position with said at least one shear rate comprises detecting shear rate of the blood flow at at least one position in the cardiovascular system of the living being and multiplying said determined viscosity of the circulating blood with said detected shear rate at said at least one position.

3. The method of claim 1 further comprising the step of determining the viscosities being experienced by the circulating blood in a selected blood vessel of the living being, said step of determining the viscosities comprising:

(a) determining a flow rate of the circulating blood through the selected blood vessel as function of time;

(b) selecting a model for the pulsation of the blood vessel that reflects compliance properties in the selected blood vessel;

(c) determining a cyclic rheological profile function for the blood vessel in terms of said characteristic blood viscosity-shear rate relationship, said flow rate and said model for the pulsation of the selected blood vessel; and (d) determining an average cyclic viscosity of the blood vessel by integrating said cyclic rheological profile function.

4. The method of claim 3 wherein said step of determining a flow rate of the circulating blood through the selected blood vessel as a function of time comprises:

(a) deriving a pulse pressure function, P(t), for the selected blood vessel which represents the pressure in the selected blood vessel over a cardiac cycle;

(b) expressing said flow rate, y(t), in terms of said pulse pressure function using a Windkessel model:

$$y(t) = CP(t) + \frac{P(t)}{R}$$

where $$C = \frac{y_s P_d - y_d P_s}{\dot{P}_s P_d - \dot{P}_d P_s}$$

$$R = \frac{\dot{P}_s P_d - \dot{P}_d P_s}{y_d \dot{P}_s - y_s \dot{P}_d}$$

and where

- $y_s$ is the velocity of the circulating blood in the selected blood vessel at systole;
- $y_d$ is the velocity of the circulating blood in the selected blood vessel at diastole;
- $P_d$ is the pressure in the selected blood vessel at diastole;
- $P_s$ is the pressure in the selected blood vessel at systole;
- $\dot{P}(t)$ is the time rate of change of the pulse pressure function;
- $\dot{P}_d$ is the time rate of change of $P_d$; and
- $\dot{P}_s$ is the time rate of change of $P_s$.

5. The method of claim 4 wherein said step of using a pulse pressure function, P(t), comprises obtaining pulse pressure data of the selected blood vessel using a pressure pulse device.

6. The method of claim 5 wherein said step of determining a model for the pulsation of the selected blood vessel comprises:

$$R(t) = a_3 \left[ 1 - a_4 \left( \frac{P(t)}{P_s} \right)^\beta \right], \text{ for } 1 < \beta < 2$$

where

- R(t) represents the changing radius of the blood vessel over time due to the pulsation of the selected blood vessel;

$$a_3 = \frac{R_d}{\theta} \cdot \frac{\omega^\theta - \theta}{\omega^\theta - 1}$$

$$a_4 = \frac{1 - \theta}{\omega^\theta - \theta}$$

where

- $R_d$ is the diastolic radius of the blood vessel;
- $\omega$ is a ratio of the diastolic blood vessel pressure to the systolic blood vessel pressure; and $\theta$ is a ratio of the diastolic radius of the blood vessel to the systolic radius of the blood vessel.

7. The method of claim 6 wherein said step of determining an average cyclic viscosity, $\eta_{ave}^a$, comprises:

$$\eta_{ave}^a = a_3 + \frac{2a_3}{T_0} \int_0^{T_0} \frac{dt}{\Lambda(k^{-3} y(t))} + \frac{a_3}{T_0} \int_0^{T_0} \frac{dt}{\Lambda(k^{-3} y(t))^2}$$

where $T_0$ is the length of a cardiac cycle of the living being;

$$k = \frac{R(t)}{R_c},$$

where $R_c$ is the radius of said capillary tube; and $$\Lambda(y) = \frac{1}{\sqrt{CT(y)}} - 1; \text{ and}$$

where CT(y) represents a Casson transform function that permits the shear stress, $\tau$, of the blood to be calculated for each time, t, in the cardiac cycle.

* * * * *